US012779223B2

(12) United States Patent
Shrivastav et al.

(10) Patent No.: US 12,779,223 B2
(45) Date of Patent: Nov. 3, 2026

(54) PERSONALIZED MACHINE LEARNING ALGORITHM FOR STIMULATION/BLOCK THERAPY FOR TREATMENT OF TYPE 2 DIABETES

(71) Applicant: Medtronic, Inc., Minneapolis, MN (US)

(72) Inventors: Maneesh Shrivastav, Blaine, MN (US); ShaileshKumar V. Musley, Brooklyn Park, MN (US); Kanthaiah Koka, Valencia, CA (US); Steven M. Goetz, North Oaks, MN (US); Suryakiran Vadrevu, Santa Clarita, CA (US); Rebecca K. Gottlieb, Culver City, CA (US); David John Miller, Austin, TX (US); Leonid M. Litvak, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 648 days.

(21) Appl. No.: 18/132,204

(22) Filed: Apr. 7, 2023

(65) Prior Publication Data

US 2023/0355141 A1 Nov. 9, 2023

Related U.S. Application Data

(60) Provisional application No. 63/342,945, filed on May 17, 2022, provisional application No. 63/342,967,
(Continued)

(51) Int. Cl.
*A61N 1/36* (2006.01)
*A61B 5/00* (2006.01)
(Continued)

(52) U.S. Cl.
CPC ...... *A61N 1/36053* (2013.01); *A61B 5/14532* (2013.01); *A61B 5/7435* (2013.01);
(Continued)

(58) Field of Classification Search
None
See application file for complete search history.

(56) References Cited

U.S. PATENT DOCUMENTS

| | | | |
|---|---|---|---|
| 4,602,624 | A | 7/1986 | Naples et al. |
| 4,926,874 | A | 5/1990 | Lee |

(Continued)

FOREIGN PATENT DOCUMENTS

| | | |
|---|---|---|
| CN | 101401314 | 4/2009 |
| WO | WO 2017/115368 | 7/2017 |

(Continued)

OTHER PUBLICATIONS

Aune et al. "Diabetes mellitus and the risk of sudden cardiac death: a systematic review and meta-analysis of prospective studies," Nutrition, Metabolism and Cardiovascular Diseases, 2018, vol. 28, pp. 543-556.

(Continued)

*Primary Examiner* — Manolis Pahakis
(74) *Attorney, Agent, or Firm* — Sheridan Ross PC

(57) ABSTRACT

A system is provided herein for stimulating an anatomical element of a patient. For example, the system may include a device (e.g., an implantable pulse generator) and an electrode device electrically coupled to the device. In some examples, the device may be configured to generate a current that is to be applied to the anatomical element via the electrode device to stimulate the anatomical element as part of a therapy aimed at achieving or supporting glycemic control in the patient. Additionally, the current may be applied to the anatomical element based on a machine
(Continued)

learning algorithm that uses inputs gathered for determining one or more characteristics for the current. Accordingly, the machine learning algorithm may be configured to determine the one or more characteristics for the current specific to the patient (e.g., to provide personalized therapy settings for the patient).

20 Claims, 6 Drawing Sheets

Related U.S. Application Data filed on May 17, 2022, provisional application No. 63/342,998, filed on May 17, 2022, provisional application No. 63/339,049, filed on May 6, 2022, provisional application No. 63/339,024, filed on May 6, 2022, provisional application No. 63/339,101, filed on May 6, 2022, provisional application No. 63/339,136, filed on May 6, 2022, provisional application No. 63/339,304, filed on May 6, 2022, provisional application No. 63/339,160, filed on May 6, 2022, provisional application No. 63/339,154, filed on May 6, 2022, provisional application No. 63/338,794, filed on May 5, 2022, provisional application No. 63/338,817, filed on May 5, 2022, provisional application No. 63/338,806, filed on May 5, 2022.

(51) Int. Cl.

| | |
|---|---|
| ***A61B 5/145*** | (2006.01) |
| ***A61B 17/00*** | (2006.01) |
| ***A61B 17/135*** | (2006.01) |
| ***A61N 1/02*** | (2006.01) |
| ***A61N 1/05*** | (2006.01) |
| ***A61N 1/372*** | (2006.01) |
| ***G16H 10/40*** | (2018.01) |
| ***G16H 20/17*** | (2018.01) |

(52) U.S. Cl.

CPC .......... *A61B 17/1355* (2013.01); *A61N 1/025* (2013.01); *A61N 1/0507* (2013.01); *A61N 1/0551* (2013.01); *A61N 1/0556* (2013.01); *A61N 1/0558* (2013.01); *A61N 1/36007* (2013.01); *A61N 1/3606* (2013.01); *A61N 1/36132* (2013.01); *A61N 1/36135* (2013.01); *A61N 1/36139* (2013.01); *A61N 1/36146* (2013.01); *A61N 1/36171* (2013.01); *A61N 1/36185* (2013.01); *A61N 1/37247* (2013.01); *G16H 10/40* (2018.01); *G16H 20/17* (2018.01); *A61B 2017/00867* (2013.01); *A61N 1/3605* (2013.01)

(56) References Cited

U.S. PATENT DOCUMENTS

| | | | | |
|---|---|---|---|---|
| 5,487,756 | A | 1/1996 | Kallesoe et al. | |
| 6,572,543 | B1 | 6/2003 | Christopherson et al. | |
| 7,069,078 | B2 | 6/2006 | Houben | |
| 7,369,897 | B2 | 5/2008 | Boveja et al. | |
| 7,702,386 | B2 | 4/2010 | Dobak et al. | |
| 7,818,069 | B2 | 10/2010 | Colborn et al. | |
| 8,244,347 | B2 | 8/2012 | Lozano | |
| 8,340,760 | B2 | 12/2012 | Dobak, III | |
| 8,428,719 | B2 | 4/2013 | Napadow | |
| 8,868,211 | B2 | 10/2014 | Durand et al. | |
| 9,033,969 | B2 | 5/2015 | Azamian et al. | |
| 9,833,621 | B2 | 12/2017 | Levine | |
| 9,937,344 | B2 | 4/2018 | Starkebaum et al. | |
| 9,974,955 | B2 | 5/2018 | Thornton et al. | |
| 10,292,596 | B2 | 5/2019 | Shadforth et al. | |
| 10,750,994 | B2 | 8/2020 | Annoni et al. | |
| 10,856,926 | B2 | 12/2020 | Azamian et al. | |
| 11,191,966 | B2 | 12/2021 | Wah | |
| 2006/0282145 | A1 | 12/2006 | Caparso et al. | |
| 2008/0039904 | A1 | 2/2008 | Bulkes et al. | |
| 2008/0046055 | A1 | 2/2008 | Durand et al. | |
| 2008/0154177 | A1 | 6/2008 | Moubayed et al. | |
| 2008/0215101 | A1 | 9/2008 | Rezai et al. | |
| 2008/0234780 | A1 | 9/2008 | Smith et al. | |
| 2009/0254143 | A1 | 10/2009 | Tweden et al. | |
| 2010/0210955 | A1 | 8/2010 | Forsell | |
| 2011/0147046 | A1 | 6/2011 | Bonde et al. | |
| 2011/0264116 | A1 | 10/2011 | Kocur et al. | |
| 2011/0301408 | A1 | 12/2011 | Augarten | |
| 2013/0165994 | A1 | 6/2013 | Ternes et al. | |
| 2014/0074188 | A1 | 3/2014 | Armstrong et al. | |
| 2014/0228900 | A1 | 8/2014 | Osorio | |
| 2015/0045850 | A1 | 2/2015 | Bork et al. | |
| 2015/0148869 | A1 | 5/2015 | Dorvall, II et al. | |
| 2015/0328464 | A1 | 11/2015 | Henry et al. | |
| 2015/0374296 | A1 | 12/2015 | Baru et al. | |
| 2016/0114165 | A1 | 4/2016 | Levine et al. | |
| 2017/0164876 | A1 | 6/2017 | Hyde et al. | |
| 2018/0085580 | A1 | 3/2018 | Perez et al. | |
| 2018/0104500 | A1* | 4/2018 | Blum | A61N 1/36125 |
| 2018/0125689 | A1 | 5/2018 | Perez et al. | |
| 2018/0303648 | A1 | 10/2018 | Mische | |
| 2018/0326162 | A1 | 11/2018 | Bral | |
| 2019/0125226 | A1* | 5/2019 | Koya | A61B 5/4839 |
| 2019/0125227 | A1 | 5/2019 | Koya et al. | |
| 2019/0174891 | A1 | 6/2019 | Nieves | |
| 2019/0175915 | A1 | 6/2019 | Brill et al. | |
| 2019/0192851 | A1 | 6/2019 | Possover | |
| 2019/0329040 | A1 | 10/2019 | Mustakos et al. | |
| 2019/0339224 | A1 | 11/2019 | Bhavaraju et al. | |
| 2020/0206496 | A1 | 7/2020 | Meng | |
| 2020/0230400 | A1 | 7/2020 | Shepard et al. | |
| 2020/0230412 | A1 | 7/2020 | Rondoini et al. | |
| 2020/0254259 | A1 | 8/2020 | Libbus et al. | |
| 2021/0146136 | A1 | 5/2021 | Waataja et al. | |
| 2021/0244949 | A1 | 8/2021 | Soin | |
| 2021/0275819 | A1 | 9/2021 | Boor et al. | |
| 2021/0290949 | A1 | 9/2021 | Holinski | |
| 2022/0062621 | A1* | 3/2022 | Hogg | A61N 1/36014 |
| 2022/0193414 | A1 | 6/2022 | Waataja et al. | |
| 2023/0000447 | A1* | 1/2023 | Mikhno | G16H 20/60 |

FOREIGN PATENT DOCUMENTS

| | | |
|---|---|---|
| WO | WO 2020/214982 | 10/2020 |
| WO | WO 2020/252428 | 12/2020 |
| WO | WO 2020/254795 | 12/2020 |
| WO | WO 2021/119741 | 6/2021 |

OTHER PUBLICATIONS

Bergner et al. "Diabetes mellitus and sudden cardiac death," Cardiology Journal, 2010, vol. 17, No. 2, pp. 117-129.
Chow et al. "Risk of Cardiac Arrhythmias During Hypoglycemia in Patients with Type 2 Diabetes and Cardiovascular Risk," Diabetes, May 2014, vol. 63, No. 5, pp. 1738-1747.
Hanefeld et al. "Hypoglycemia and Cardiovascular Risk: Is There a Major Link?" Diabetes Care, 2016, vol. 39, Suppl. 2, pp. S205-S209.
Hirotani et al. "Carbon Nanotube Thin Films for High-Performance Flexible Electronics Applications," Topics in Current Chemistry, Jan. 2019, vol. 377, No. 1, Article No. 3.
Hsieh et al. "The enigma of the dead-in-bed syndrome: challenges in predicting and preventing this devastating complication of type 1 diabetes," Journal of Diabetes and its Complications, 2014, vol. 28, pp. 585-587.
Jones et al. "Neuromodulation using ultra low frequency current waveform reversibly blocks axonal conduction and chronic pain," Science Translational Medicine, Aug. 2021, vol. 13, No. 608, article eabg9890.

(56) References Cited

OTHER PUBLICATIONS

Jovanov et al. "Sensors and Systems for Obesity Care and Research," IEEE, 36th Annual International Conference of the IEEE Engineering in Medicine and Biology Society, Aug. 2014, pp. 3188-3191.
Murastov et al. "Flexible and water-stable graphene-based electrodes for long-term use in bioelectronics," Biosensors and Bioelectronics, Oct. 2020, vol. 166, Article 112426.
Shapiro et al. Pudendal Nerve Block by Low-Frequency (≤1 kHz) Biphasic Electrical Stimulation, Neuromodulations, Aug. 2021, vol. 24, No. 6, pp. 1012-1017.
Tancredi et al. "Excess Mortality among Persons with Type 2 Diabetes," The New England Journal of Medicine, 2015, vol. 373, pp. 1720-1732.
Yi et al. "The role of the autonomic nervous liver innervation in the control of energy metabolism," Biochimica et Biophysica Acta, Apr. 2010, vol. 1802, No. 4, pp. 416-431.
Zaccardi et al. "Diabetes mellitus and risk of sudden cardiac death," International Journal of Cardiology, Dec. 2014, vol. 177, No. 2, pp. 535-537.
International Search Report and Written Opinion for International (PCT) Patent Application No. PCT/US2023/065510, dated Jul. 11, 2023 10 pages.
International Search Report and Written Opinion for International (PCT) Patent Application No. PCT/US2023/065428, dated Jul. 20, 2023 12 pages.
International Preliminary Report on Patentability for International (PCT) Patent Application No. PCT/US2023/065510, dated Nov. 14, 2024 7 pages.
International Preliminary Report on Patentability for International (PCT) Patent Application No. PCT/US2023/065428, dated Nov. 14, 2024 8 pages.
Official Action for U.S. Appl. No. 18/131,500, dated May 21, 2025 6 pages Restriction Requirement.
Official Action for U.S. Appl. No. 18/131,500, dated Jul. 28, 2025 10 pages.
Official Action for U.S. Appl. No. 18/131,513, dated Jun. 4, 2025 12 pages.
Official Action for U.S. Appl. No. 18/131,542, dated Jul. 3, 2025 21 pages.
Official Action for U.S. Appl. No. 18/131,542, dated Oct. 24, 2025 24 pages.
Official Action for U.S. Appl. No. 18/131,555, dated Jul. 24, 2025 6 pages Restriction Requirement.
Official Action for U.S. Appl. No. 18/131,555, dated Aug. 14, 2025 14 pages.
Official Action for U.S. Appl. No. 18/131,555, dated Oct. 24, 2025 16 pages.
Official Action for U.S. Appl. No. 18/131,576, dated Jun. 20, 2025 22 pages.
Official Action for U.S. Appl. No. 18/131,576, dated Oct. 7, 2025 20 pages.
Official Action for U.S. Appl. No. 18/131,592, dated Jun. 11, 2025 15 pages.
Official Action for U.S. Appl. No. 18/131,592, dated Sep. 19, 2025 19 pages.
Official Action for U.S. Appl. No. 18/132,186, dated Aug. 19, 2025 24 pages.
Official Action for U.S. Appl. No. 18/131,614, dated Sep. 17, 2025 8 pages.
Official Action for U.S. Appl. No. 18/132,219, dated Jun. 30, 2025 16 pages.
Official Action for U.S. Appl. No. 18/132,232, dated Jul. 17, 2025 20 pages.
Official Action for European Patent Application No. 23721235.2, dated Oct. 23, 2025, 4 pages.
Official Action for U.S. Appl. No. 18/131,500, dated Jan. 8, 2026 11 pages.
Official Action for U.S. Appl. No. 18/131,513, dated Dec. 10, 2025 11 pages.
Notice of Allowance for U.S. Appl. No. 18/132,219, dated Nov. 13, 2025 11 pages.
Official Action for U.S. Appl. No. 18/132,232, dated Nov. 21, 2025 28 pages.
Notice of Allowance for U.S. Appl. No. 18/131,513, dated Apr. 3, 2026 8 pages.
Official Action for U.S. Appl. No. 18/131,542, dated Mar. 10, 2026 25 pages.
Official Action for U.S. Appl. No. 18/131,555, dated Mar. 12, 2026 16 pages.
Notice of Allowance for U.S. Appl. No. 18/131,576, dated Mar. 11, 2026 8 pages.
Official Action for U.S. Appl. No. 18/132,186, dated Mar. 4, 2026 26 pages.
Official Action for U.S. Appl. No. 18/131,614, dated Apr. 9, 2026 11 pages.

* cited by examiner

PERSONALIZED MACHINE LEARNING ALGORITHM FOR STIMULATION/BLOCK THERAPY FOR TREATMENT OF TYPE 2 DIABETES

CROSS REFERENCE TO RELATED APPLICATIONS

This application claims the benefit of U.S. Provisional Application No. 63/339,154, filed on May 6, 2022, entitled "Personalized Machine Learning Algorithm for Stimulation/Block Therapy for Treatment of Type 2 Diabetes"; U.S. Provisional Application No. 63/338,794, filed on May 5, 2022, entitled "Systems and Methods for Stimulating an Anatomical Element Using an Electrode Device"; U.S. Provisional Application No. 63/339,049, filed on May 6, 2022, entitled "Systems and Methods for Mechanically Blocking a Nerve"; U.S. Provisional Application No. 63/338,806, filed on May 5, 2022, entitled "Systems and Methods for Wirelessly Stimulating or Blocking at Least One Nerve"; U.S. Provisional Application No. 63/339, 101, filed on May 6, 2022,entitled "Neuromodulation Techniques to Create a Nerve Blockage with a Combination Stimulation/Block Therapy for Glycemic Control"; U.S. Provisional Application No. 63/339, 136, filed on May 6, 2022, entitled "Neuromodulation for Treatment of Neonatal Chronic Hyperinsulinism"; U.S. Provisional Application No. 63/342, 945, filed on May 17,2022, entitled "Neuromodulation Techniques for Treatment of Hypoglycemia"; U.S. Provisional Application No. 63/342,998, filed on May 17, 2022, entitled "Closed-Loop Feedback and Treatment"; U.S. Provisional Application No. 63/338,817, filed on May 5,2022, entitled "Systems and Methods for Monitoring and Controlling an Implantable Pulse Generator"; U.S. Provisional Application No. 63/339,024, filed on May 6, 2022,entitled "Programming and Calibration of Closed-Loop Vagal Nerve Stimulation Device"; U.S. Provisional Application No. 63/339, 304, filed on May 6, 2022, entitled "Systems and Methods for Stimulating or Blocking a Nerve Using an Electrode Device with a Sutureless Closure"; U.S. Provisional Application No. 63/342,967, filed on May 17,2022, entitled "Patient User Interface for a Stimulation/Block Therapy for Treatment of Type 2 Diabetes"; and U.S. Provisional Application No. 63/339,160, filed on May 6,2022, entitled "Utilization of Growth Curves for Optimization of Type 2 Diabetes Treatment", all of which applications are incorporated herein by reference in their entireties.

BACKGROUND

The present disclosure is generally directed to therapeutic neuromodulation and relates more particularly to a stimulation/block therapy to affect glycemic control of a patient.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic.

BRIEF SUMMARY

Example aspects of the present disclosure include:

A system for stimulating an anatomical element of a patient, comprising: an implantable pulse generator configured to generate a current; an electrode device electrically coupled to the implantable pulse generator, the electrode device comprising a plurality of electrodes configured for placement on or around the anatomical element of the patient; a processor; and a memory storing data for processing by the processor, the data, when processed, causes the processor to: transmit instructions to the implantable pulse generator to apply the current to the anatomical element of the patient via the plurality of electrodes of the electrode device, wherein the current is applied to the anatomical element based at least in part on a machine learning algorithm that uses inputs gathered for determining one or more characteristics for the current.

Any of the aspects herein, wherein the memory stores further data for processing by the processor that, when processed, causes the processor to: measure a first glycemic response for the patient, the first glycemic response corresponding to a first set of inputs at a first instance in time; and determine, using the machine learning algorithm, the one or more characteristics for the current based at least in part on the first glycemic response.

Any of the aspects herein, wherein the memory stores further data for processing by the processor that, when processed, causes the processor to: measure a second glycemic response for the patient, the second glycemic response corresponding to a substantially similar set of inputs to the first set of inputs occurring at a second instance in time, wherein the second glycemic response is different than the first glycemic response and the second instance in time is different than the first instance in time; determine a difference between the first glycemic response and the second glycemic response; and update the machine learning algorithm to determine the one or more characteristics for the current based at least in part on the determined difference.

Any of the aspects herein, further comprising: a first user interface configured to store the machine learning algorithm, the first user interface in communication with at least the implantable pulse generator and the processor, wherein the memory stores further data for processing by the processor that, when processed, causes the processor to: receive one or more first inputs from the patient via the first user interface, wherein the one or more first inputs are used to train the machine learning algorithm to determine the one or more characteristics for the current based at least in part on a glycemic response of the patient corresponding to the one or more first inputs; and transmit the one or more characteristics for the current to the implantable pulse generator, wherein the current is applied to the anatomical element based at least in part on transmitting the one or more characteristics.

Any of the aspects herein, further comprising: a second user interface accessible by a clinical professional, the second user interface in communication with the first user interface, the implantable pulse generator, the processor, or a combination thereof, wherein the memory stores further data for processing by the processor that, when processed, causes the processor to: receive one or more settings for applying the current to the anatomical element from the clinical professional via the second user interface; and transmit the one or more settings to the implantable pulse generator, wherein the current is applied to the anatomical element based at least in part on transmitting the one or more settings.

Any of the aspects herein, wherein the one or more first inputs comprise a level of patient satisfaction with the current that is applied based at least in part on the one or more characteristics, a level of patient comfort with the current that is applied based at least in part on the one or more characteristics, a time of day when the patient ingests a meal, a type of food ingested with the meal, an amount of activity levels for the patient, results of an A1C test for the patient, additional medication dosages used by the patient, or a combination thereof.

Any of the aspects herein, further comprising: a monitoring device configured to continuously monitor glucose levels in the patient, wherein the memory stores further data for processing by the processor that, when processed, causes the processor to: receive one or more outputs from the monitoring device, wherein the one or more characteristics for the current are determined from the machine learning algorithm based at least in part on the one or more outputs received from the monitoring device.

Any of the aspects herein, wherein the one or more outputs received from the monitoring device comprise an average reduction in post prandial glycemic peak given a known intake of carbohydrates, instantaneous glucose measurements, temporal glucose trends, glucose time in range, insulin sensitivity of the patient, a slope or time for a glycemic response of the patient to come within an acceptable range after the current is applied to the anatomical element, a duration of applying the current to the anatomical element to effect a desirable glycemic response, or a combination thereof.

Any of the aspects herein, wherein the one or more characteristics of the current determined by the machine learning algorithm comprise an optimized frequency, amplitude, pulse width, shape of a waveform, slope for ramp up, slope for ramp down, pattern, duty cycle, or a combination thereof for the current.

Any of the aspects herein, wherein the one or more characteristics for the current are determined specific to the patient.

Any of the aspects herein, wherein the machine learning algorithm comprises a fast train machine learning model, a linear regression model, or a combination thereof.

Any of the aspects herein, wherein the anatomical element comprises a celiac vagal trunk and a hepatic vagal trunk of the patient.

Any of the aspects herein, wherein the current being applied to the anatomical element reduces a glycemic response in the patient.

A system for stimulating an anatomical element of a patient, comprising: an implantable pulse generator configured to generate a current; an electrode device comprising: a body and a plurality of electrodes disposed on the body and configured to apply the current to the anatomical element; a processor; and a memory storing data for processing by the processor, the data, when processed, causes the processor to: transmit instructions to the implantable pulse generator to apply the current to the anatomical element of the patient via the plurality of electrodes of the electrode device, wherein the current is applied to the anatomical element based at least in part on a machine learning algorithm that uses inputs gathered for determining one or more characteristics for the current.

Any of the aspects herein, wherein the memory stores further data for processing by the processor that, when processed, causes the processor to: measure a first glycemic response for the patient, the first glycemic response corresponding to a first set of inputs at a first instance in time; and determine, using the machine learning algorithm, the one or more characteristics for the current based at least in part on the first glycemic response.

Any of the aspects herein, wherein the memory stores further data for processing by the processor that, when processed, causes the processor to: measure a second glycemic response for the patient, the second glycemic response corresponding to a substantially similar set of inputs to the first set of inputs occurring at a second instance in time, wherein the second glycemic response is different than the first glycemic response and the second instance in time is different than the first instance in time; determine a difference between the first glycemic response and the second glycemic response; and update the machine learning algorithm to determine the one or more characteristics for the current based at least in part on the determined difference.

Any of the aspects herein, further comprising: a first user interface configured to store the machine learning algorithm, the first user interface in communication with at least the implantable pulse generator and the processor, wherein the memory stores further data for processing by the processor that, when processed, causes the processor to: receive one or more first inputs from the patient via the first user interface, wherein the one or more first inputs are used to train the machine learning algorithm to determine the one or more characteristics for the current based at least in part on a glycemic response of the patient corresponding to the one or more first inputs; and transmit the one or more characteristics for the current to the implantable pulse generator, wherein the current is applied to the anatomical element based at least in part on transmitting the one or more characteristics.

Any of the aspects herein, further comprising: a second user interface accessible by a clinical professional, the second user interface in communication with the first user interface, the implantable pulse generator, the processor, or a combination thereof, wherein the memory stores further data for processing by the processor that, when processed, causes the processor to: receive one or more settings for applying the current to the anatomical element from the clinical professional via the second user interface; and transmit the one or more settings to the implantable pulse generator, wherein the current is applied to the anatomical element based at least in part on transmitting the one or more settings.

A system for stimulating an anatomical element of a patient, comprising: an implantable pulse generator configured to generate a current; and an electrode device comprising: a body and a plurality of electrodes disposed on the body and configured to apply the current to the anatomical element, wherein the current is applied to the anatomical element based at least in part on a machine learning algorithm that uses inputs gathered for determining one or more characteristics for the current.

Any of the aspects herein, further comprising: a first user interface configured to store the machine learning algorithm, the first user interface accessible by the patient to provide inputs for training the machine learning algorithm; and a second user interface accessible by a clinical professional, wherein the clinical professional provides settings via the second user interface for training the machine learning algorithm, determining the one or more characteristics of the current, or a combination thereof.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

Figure 1:
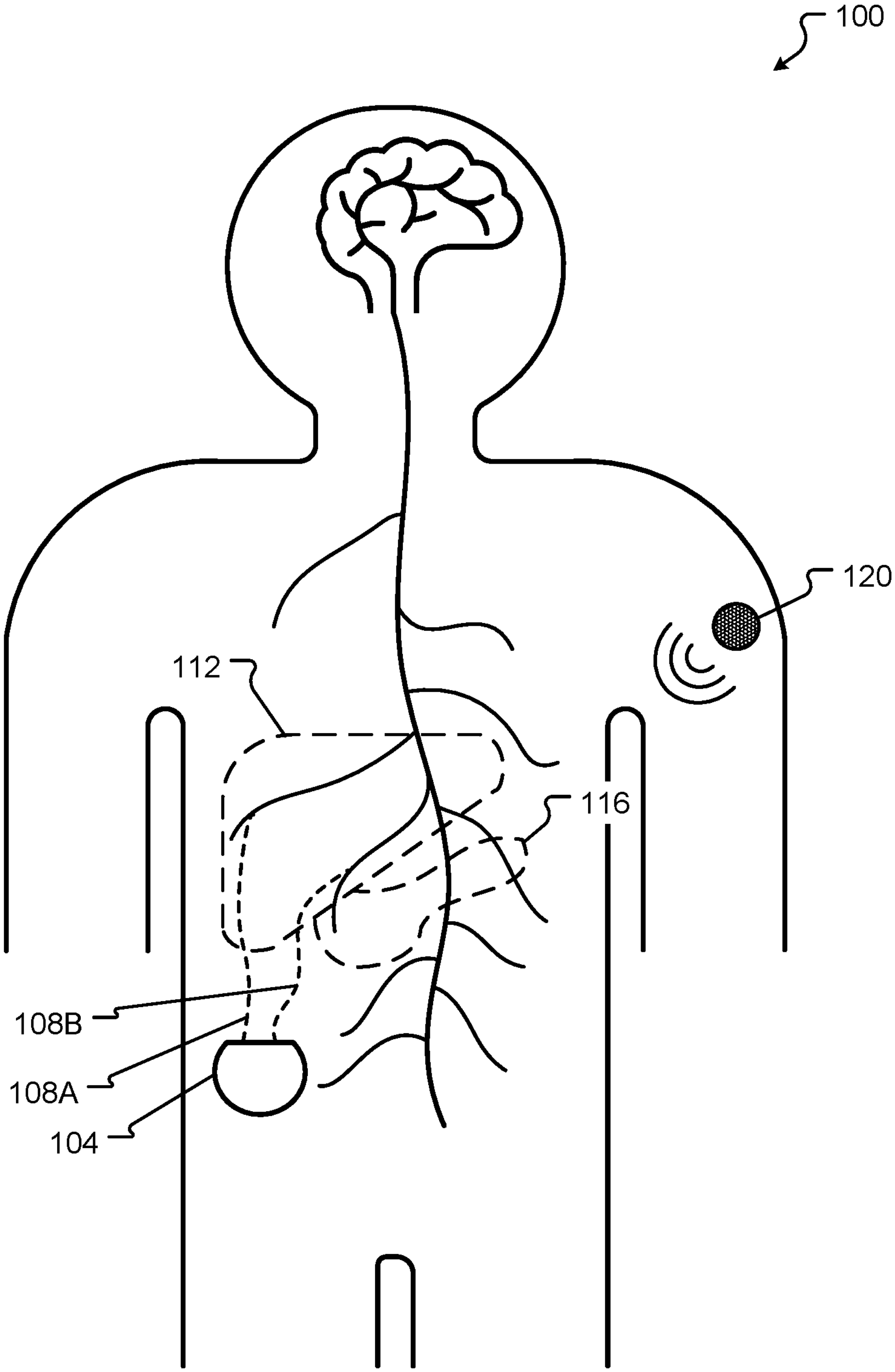
FIG. 1 is a diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., random-access memory (RAM), read-only memory (ROM), electrically erasable programmable ROM (EEPROM), flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements. The processors listed herein are not intended to be an exhaustive list of all possible processors that can be used for implementation of the described techniques, and any future iterations of such chips, technologies, or processors may be used to implement the techniques and embodiments of the present disclosure as described herein.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

Vagus nerve stimulation (VNS) is a technology that has been developed to treat different disorders or ailments of a patient, such as epilepsy and depression. In some examples, VNS involves placing a device in or on a patient's body that uses electrical impulses to stimulate the vagus nerve. For example, the device may be usually placed under the skin of the patient, where a wire (e.g., lead) and/or electrode connects the device to the vagus nerve. Once the device is activated, the device sends signals through the vagus nerve to the patient's brainstem (e.g., or different target area in the patient, such as other organs of the patient), transmitting information to their brain. For example, with VNS, the device may be configured to send regular, mild pulses of electrical energy to the brain via the vagus nerve. In some examples, the device may be referred to as an implantable pulse generator. An implantable vagus nerve stimulator has been approved to treat epilepsy and depression in qualifying patients.

The vagus nerve (e.g., also called the pneumogastric nerve, vagal nerve, the cranial nerve X, etc.) is responsible for various internal organ functions of a patient, including digestion, heart rate, breathing, cardiovascular activity, and reflex actions (e.g., coughing, sneezing, swallowing, and vomiting). Most patients may have one vagus nerve on each side of their body, with numerous branches running from their brainstem through their neck, chest, and abdomen down to part of their colon. The vagus nerve plays a role in many bodily functions and may form a link between different areas of the patient, such as the brain and the gut. The vagus nerve is a critical nerve for supplying parasympathetic information to the visceral organs of the respiratory, digestive, and urinary systems. Additionally, the vagus nerve is important in the control of heart rate, bronchoconstriction, and digestive processes. In some cases, the vagus nerve may be considered a mixed nerve based on including both afferent (sensory) fibers and efferent (motor) fibers. As such, based on including the two types of fibers, the vagus nerve may be responsible for carrying motor signals to organs for innervating the organs (e.g., via the efferent fibers), as well as carrying sensory information from the organs back to the brain (e.g., via the afferent fibers).

The vagus nerve has a number of different functions. Four key functions of the vagus nerve are carrying sensory signals, carrying special sensory signals, providing motor functions, and assisting in parasympathetic functions. For example, the sensory signals carried by the vagus nerve may include signaling between the brain and the throat, heart, lungs, and abdomen. The special sensory signals carried by the vagus nerve may provide signaling of special senses in the patient, such as the taste sensation behind the tongue. Additionally, the vagus nerve may enable certain motor functions of the patient, such as providing movement functions for muscles in the neck responsible for swallowing and speech. The parasympathetic functions provided by the vagus nerve may include digestive tract, respiration, and heart rate functioning. In some cases, the nervous system can be divided into two areas: sympathetic and parasympathetic. The sympathetic side increases alertness, energy, blood pressure, heart rate, and breathing rate. The parasympathetic side, which the vagus nerve is heavily involved in, decreases alertness, blood pressure, and heart rate, and helps with calmness, relaxation, and digestion.

VNS is considered a type of neuromodulation (e.g., a technology that acts directly upon nerves of a patient, such as the alteration, or "modulation," of nerve activity by delivering electrical impulses or pharmaceutical agents directly to a target area). For example, as described above, VNS may include using a device (e.g., implanted in a patient or attached to the patient) that is configured to send regular, mild pulses of electrical energy to a target area of the patient (e.g., brainstem, organ, etc.) via the vagus nerve. The electrical pulses or impulses may affect how that target area of the patient functions to potentially treat different disorders or ailments of a patient.

In some examples, for epileptic patients that suffer from seizures, VNS may change how brain cells work by applying electrical stimulation to certain areas involved in seizures. For example, research has shown that VNS may help control seizures by increasing blood flow in key areas, raising levels of some brain substances (e.g., neurotransmitters) important to control seizures, changing electroencephalogram (EEG) patterns during a seizure, etc. As an example, an epileptic patient's heart rate may increase during a seizure or epileptic episode, so the VNS device may be programmed to send stimulation to the vagus nerve regular intervals and when periods of increased heart rate are seen, where applying stimulation at those times of increased heart rate may help stop seizures. Additionally or alternatively, depression has been tied to an imbalance in certain brain chemicals (e.g., neurotransmitters), so VNS is believed to assist in treating patients diagnosed with depression by using electricity (e.g., electrical pulses/impulses) to influence the production of those brain chemicals.

Diabetes represents a large and growing global health issue with estimates of over 537 million patients worldwide having been diagnosed with type 2 diabetes and estimates of 6.7 million annual deaths related to complications of diabetes. Despite different types of treatments being developed and utilized (e.g., medication, surgery, diet, etc.), type 2 diabetes remains challenging to effectively treat. Type 2 patients must frequently contend with keeping their blood sugar levels in a desirable glycemic range. Prolonged deviations can lead to long term complications such as retinopathy, nephropathy (e.g., kidney damage), cardiovascular disease, etc. Because treatment for diabetes is self-managed by the patient on a day-to-day basis (e.g., the patients self-inject the insulin), compliance or adherence with treatments can be problematic. Additionally, in a financial sense, global expenditures for type 2 diabetes treatments, preventive measures, and resulting consequences are estimated at about $966 billion per year. Compounding this issue of high global expenditures is the increasing price of insulin.

As described herein, a neuromodulation technique is provided for glycemic control (e.g., as a treatment for diabetes) using a stimulation/block therapy (e.g., type of VNS). For example, the neuromodulation technique may generally include using a device (e.g., including at least an implantable pulse generator) to provide electrical stimulation (e.g., electrical pulses/impulses) on one or more trunks of the vagus nerve (e.g., vagal trunks) to mute a glycemic response for patients with diabetes. The "patient" as used herein may refer to *Homo sapiens* or any other living being that has a vagus nerve.

In some examples, the device may provide stimulation/blocking of the celiac and hepatic vagal trunks (e.g., using the device) for the purposes of glycemic control. For example, the anterior sub diaphragmatic vagal trunk at the hepatic branching point of the vagus nerve may be electrically blocked (e.g., down-regulated) by delivering a high frequency stimulation (e.g., of about 5 kilohertz (kHz) or in a range between 1 kHz to 50 kHz). Additionally or alternatively, the posterior sub diaphragmatic vagal trunk at the celiac branching point of the vagus nerve may be electrically stimulated (e.g., up-regulated) by delivering a low frequency stimulation (e.g., a square wave at 1 Hz or within a range from 0.1 to 20 Hz). In some examples, the electrical blocking and/or electrical stimulating of the respective vagal trunks may be performed by using one or more cuff electrodes (e.g., of the device) placed on the corresponding vagal trunks (e.g., sutured or otherwise held in place). The desired response by providing the stimulation/block therapy is a muting of the glycemic response of a patient. In some examples, muting of the glycemic response may refer to a lower post prandial peak of the glycemic response as compared to a peak without the stimulation/block therapy being applied.

Using the stimulation/block therapy to achieve a muting of the glycemic response is advantageous for those with type 2 diabetes where the postprandial glycemic response (e.g., occurring after a meal) can be very high. For example, some patients with type 2 diabetes may have high blood sugar levels (e.g., glucose levels) after eating a meal based on their reduced or lack of insulin production (e.g., normal insulin production in the body lowers blood sugar levels postprandially by promoting absorption of glucose from the blood into different cells). Additionally or alternatively, patients diagnosed with type 2 diabetes may generally have high glycemic levels at different points of the day (e.g., not necessarily postprandially or immediately after a meal). Over time, the effect of high glycemic values can have a detrimental effect on one's health, leading to neuropathy, retinopathy, and other ailments. Accordingly, by using the stimulation/block therapy provided herein, a high glycemic response experienced by type 2 diabetes patients may be muted (e.g., the glycemic response is reduced, particularly post prandially). Additionally, the therapy aims to improve insulin sensitivity by blocking hepatic glucose production and also by stimulating pancreatic insulin production needed for glycemic control, where the lack of insulin sensitivity can potentially lead to an imbalance in glycemic control and consequent systemic complications in patients with type 2 diabetes. In some examples, the therapy may also improve fasting hyperglycemia, which can be commonly seen in patients with type 2 diabetes.

The stimulation/block therapy applied to respective vagal trunks results in a method for controlling the glycemic response of a patient. In some examples, a method may also be desired for personalizing the therapy for the individual patient. For example, personalization of the therapy may include adapting the therapy to a frequency of how often the therapy is used or applied to the patient and lifestyle specific to the patient. Accordingly, the method described herein may include using a machine learning algorithm that takes a set of inputs and continuously adapts, learns, and optimizes the output of the therapy system for the patient. In some examples, the therapy system may use a continuous glucose sensor (e.g., monitoring device that is configured to continuously monitor glucose levels in the patient) as an input to the optimization algorithm (e.g., the machine learning algorithm used to determine optimal settings or characteristics for applying the therapy). Additionally or alternatively, the therapy system may not be dependent on a continuous glucose sensor or continuous glucose monitor for inputs to the optimization algorithm and may use other implements for entering or receiving blood glucose data from the patient, such as self-monitored blood glucose measurements (e.g., taken via finger sticks).

The machine learning algorithm may optimize one or more parameters for applying the therapy per patient. For example, the one or more parameters may include an optimization of a frequency, an amplitude, a ramp up, and a pattern of stimulation for the stimulation/block therapy specific to the patient. In some examples, a duty cycle (e.g., duration of applying the therapy to achieve a desired effect) for applying the therapy may also be optimized specific to the patient based on using the machine learning algorithm. Additionally, the machine learning algorithm may adapt the therapy to lifestyle preferences of the patient, such as levels of activity, nocturnal patterns, and circadian rhythm of the patient. Additionally or alternatively, real-time and/or historical data may be used to train the machine learning algorithm and/or determine when certain operational parameters of the therapy should be adjusted. For instance, operational parameters of the therapy such as signal frequency, signal type (e.g., square wave, sinusoidal wave, triangle wave, etc.), duty cycle, treatment duration, etc. may be adjusted based on inputs such as: number of carbohydrates ingested by the patient during mealtime, medications taken by the patient, exercise/activity levels, stress, amount of sleep, microbiome content, genetic components, comorbidities, and/or macronutrients.

In some examples, for training the machine learning algorithm, the current (e.g., that is to be applied to the anatomical element as part of the stimulation/block therapy described herein) may further be tuned, by selecting specific electrodes, varying amplitude and pulsewidth of the stimulation trains, varying frequency of stimulation or block, or varying the pulse shape and pattern, so as to maximize efficacious response in a patient and minimize undesired side effects on other body systems also enervated by the vagus nerve. As an example, the direction of neural activation may be steered towards the organ of interest (liver or pancreas) by configuring the cathodic element of the stimulating array to be nearer on the nerve to the organ, the anodic element further away, and selecting a pulse shape where the anodic phase generally inhibits propagation of neural action potentials away from the target organ.

In some examples, the machine learning algorithm (e.g., artificial intelligence (AI) algorithm) may be offloaded to a user interface or application accessible by the patient (e.g., a user application), which may provide battery savings for the device that provides the stimulation/block therapy that would have otherwise stored the machine learning algorithm (e.g., an implantable pulse generator). The patient application may allow for as much or as little engagement as the patient desires. In some examples, the machine learning algorithm or component of the system described herein may be a fast train model (i.e., the use of the machine learning algorithm is intended to wean the patient off the application so that minimal interaction is required from the patient). Additionally, the therapy system may include a clinician user interface (e.g., second application that is accessible by a medical professional or clinician responsible for initializing, implanting, and/or programming the device that provides the stimulation/block therapy). In some examples, the clinician user interface may be intended to be an application-based module.

In some examples, one or more features may be utilized for training the machine learning algorithm described herein that is used to determine characteristics for optimally applying the therapy. For example, the one or more features may include one or more optimal stimulation parameters that achieve a desired level of glycemic reduction response in the patient. The one or more optimal stimulation parameters may include a frequency for the stimulation/block therapy, an amplitude for the stimulation/block therapy, sequencing or duration of stimulation/block therapy elements, a pulse width for the stimulation/block therapy, a shape of a waveform used for the stimulation/block therapy (e.g., a triangular wave, a square wave, a sine wave, a trapezoidal wave, asymmetric pulse shape, etc.), a pattern or burst of similar or different pulses, preconditioning pulses delivered prior to therapy pulses, a slope for a ramp up of the stimulation/block therapy (e.g., start with small amplitude and level off to an optimal level), a slope for a ramp down of the stimulation/block therapy (e.g., similar to the ramp up, but for termination of the therapy), or a combination thereof. Additionally or alternatively, the one or more features used to train the machine learning algorithm may include an average reduction in a post prandial glycemic peak given a known carbohydrate intake (e.g., in grams (g)).

In some examples, the patient may also provide one or more inputs to be used for the one or more features utilized for training the machine learning algorithm. For example, the patient may provide a level of patient satisfaction with current or previous parameters used when applying the therapy (e.g., as recorded via the patient-accessible application, such as via a satisfaction assessment form) and/or a level of patient comfort with current or previous parameters used when applying the therapy (e.g., as recorded via the patient-accessible application). Additionally or alternatively, the patient may provide one or more of a time of day when the patient ingests a meal, a type of food ingested with the meal (e.g., as measured by a carbohydrate count), activity levels of the patient, and results of an A1C test (e.g., a blood test for type 2 diabetes and prediabetes that measures average blood glucose or blood sugar levels in the patient over a period of time, such as over the previous three (3) months). In some cases, the events associated with the one or more inputs may be detected by a wearable device of the patient, an application (e.g., accessed via a device or mobile phone of the patient), or a different environmental sensor associated with the patient, rather than having the inputs being provided by the patient.

In some examples, one or more of the features used for training the machine learning algorithm may be determined or based on outputs received from a monitoring device used by the patient, such as a continuous glucose sensor. For example, the monitoring device may provide information for the features used to train the machine learning algorithm, such as instantaneous glucose values, temporal glucose trends, glucose time in range, insulin sensitivity of the patient, a slope (e.g., time) for the glycemic response of the patient to come within an acceptable range after the therapy is activated, additional medication dosage used by the patient or applied to the patient, a duration of stimulation required to affect a desirable response, or a combination thereof. Additionally or alternatively, one or more of the features used for training the machine learning algorithm may be determined from additional components of the therapy system provided herein, such as the patient-accessible application, the clinician user interface, or another component. Additionally, the features listed herein that are used for training the machine learning algorithm are not meant to be an exhaustive list of all features used to train the machine learning algorithm, and additional features may be used to train the machine learning algorithm not explicitly listed herein.

The machine learning algorithm used to optimize one or more parameters for applying the therapy per patient may be based on a linear regression with multiple variables. For example, Equation 1 below may represent a multivariate linear regression model on which the machine learning algorithm is based:

$$h_\theta(x)=\theta_0+x_1\theta_1+x_2\theta_2+\ldots+x_n\theta_n \quad (1)$$

Each variable x (e.g., $x_1$, $x_2$, . . . , $x_n$) may represent an individual feature used to train the machine learning algorithm, and θ may be a derived coefficient of the multivariate linear regression model.

Embodiments of the present disclosure provide technical solutions to one or more of the problems of (1) controlling a glycemic response of a patient, (2) determining optimal parameters for applying a stimulation/block therapy, (3) personalizing the stimulation/block therapy specific to a given patient, and (4) modifying a delivered therapy over time as a patient state changes or as a disease progresses.

Turning to FIG. 1, a diagram of a system 100 according to at least one embodiment of the present disclosure is shown. The system 100 may be used to provide glycemic control for a patient and/or carry out one or more other aspects of one or more of the methods disclosed herein. For example, the system 100 may include at least a device 104 that is capable of providing a stimulation/blocking therapy that mutes a glycemic response for patients with diabetes. In some examples, the device 104 may be referred to as an implantable pulse generator, an implantable neurostimulator, or another type of device not explicitly listed or described herein. Additionally, the system 100 may include one or more wires 108 (e.g., leads) that provide a connection between the device 104 and nerves of the patient for enabling the stimulation/blocking therapy.

As described previously, neuromodulation techniques (e.g., technologies that act directly upon nerves of a patient, such as the alteration, or "modulation," of nerve activity by delivering electrical impulses or localized pharmaceutical agents directly to a target area) may be used for assisting in treatments for different diseases, disorders, or ailments of a patient, such as epilepsy and depression. Accordingly, as described herein, the neuromodulation techniques may be used for muting a glycemic response in the patient to assist in the treatment of diabetes for the patient. For example, the device 104 may provide electrical stimulation to one or more trunks of the vagus nerve of the patient (e.g., via the one or more wires 108) to provide the stimulation/blocking therapy for supporting glycemic control in the patient.

In some examples, the one or more wires 108 may include at least a first wire 108A and a second wire 108B connected to respective vagal trunks (e.g., different trunks of the vagus nerve). As described previously, most patients have one vagus nerve on each side of their body, running from their brainstem through their neck, chest, and abdomen down to part of their colon. The vagus nerve plays a role in many bodily functions and may form a link between different areas of the patient, such as the brain and the gut. For example, the vagus nerve is responsible for various internal organ functions of a patient, including digestion, heart rate, breathing, cardiovascular activity, and reflex actions (e.g., coughing, sneezing, swallowing, and vomiting).

Accordingly, the first wire 108A may be connected to a first vagal trunk of the patient (e.g., the anterior sub diaphragmatic vagal trunk at the hepatic branching point of the vagus nerve) to provide an electrical blocking signal (e.g., a down-regulating signal) from the device 104 to that first vagal trunk (e.g., by delivering a high frequency stimulation, such as a given waveform at about 5 kHz). Additionally or alternatively, the second wire 108B may be connected to a second vagal trunk of the patient (e.g., the posterior sub diaphragmatic vagal trunk at the celiac branching point of the vagus nerve) to provide an electrical stimulation signal (e.g., an up-regulating signal) from the device 104 to that second vagal trunk (e.g., by delivering a low frequency stimulation, such as a square wave or other waveform at 1 Hz). By providing the electrical blocking signal and the electrical stimulation signal to the respective vagal trunks, the system 100 may provide a muting of the glycemic response of the patient when the stimulation/blocking therapy is applied. For example, muting of the glycemic response may refer to a lower post prandial peak of the glycemic response as compared to a peak without the stimulation/block therapy being applied.

In some examples, the vagal trunks to which the wires 108 are connected may be connected to or otherwise in the vicinity of one or more organs of the patient, such that the blocking/stimulation signals provided to the respective vagal trunks by the wires 108 and the device 104 are delivered to the one or more organs. For example, the first vagal trunk (e.g., to which the first wire 108A is connected) may be connected to a first organ 112 of the patient, and the second vagal trunk (e.g., to which the second wire 108B is connected) may be connected to a second organ 116. Additionally or alternatively, while the respective vagal trunks are shown as being connected to the corresponding organs of the patient as described, the vagal trunks to which the wires 108 are connected may be connected to the other organ (e.g., the first vagal trunk is connected to the second organ 116 and the second vagal trunk is connected to the first organ 112) or may be connected to different organs of the patient. In some examples, the first organ 112 may represent a liver of the patient, and the second organ 116 may represent a pancreas of the patient. In such examples, the blocking/stimulation signals provided by the wires 108 and the device 104 may be delivered to the liver and/or pancreas of the patient to mute a glycemic response of the patient as described herein.

In some examples, the wires 108 may provide the electrical signals to the respective vagal trunks via electrodes of an electrode device (e.g., cuff electrodes) that are connected to the vagal trunks (e.g., sutured in place, wrapped around the nerves of the vagal trunks, etc.). In some examples, the wires 108 may be referenced as cuff electrodes or may otherwise include the cuff electrodes (e.g., at an end of the wires 108 not connected or plugged into the device 104). Additionally or alternatively, while shown as physical wires that provide the connection between the device 104 and the one or more vagal trunks, the cuff electrodes may provide the electrical blocking and/or stimulation signals to the one or more vagal trunks wirelessly (e.g., with or without the device 104).

Additionally, while not shown, the system 100 may include one or more processors (e.g., one or more DSPs, general purpose microprocessors, graphics processing units, ASICs, FPGAs, or other equivalent integrated or discrete logic circuitry) that are programmed to carry out one or more aspects of the present disclosure. In some examples, the one or more processors may include a memory or may be otherwise configured to perform the aspects of the present disclosure. For example, the one or more processors may provide instructions to the device 104, the cuff electrodes, or other components of the system 100 not explicitly shown or described with reference to FIG. 1 for providing the stimulation/blocking therapy to promote glycemic control in a patient as described herein. In some examples, the one or more processors may be part of the device 104 or part of a control unit for the system 100 (e.g., where the control unit is in communication with the device 104 and/or other components of the system 100).

In some examples, the system 100 may also optionally include a glucose sensor 120 that communicates (e.g., wirelessly) with other components of the system 100 (e.g., the device 104, the one or more processors, etc.) to achieve better glycemic control in the patient. For example, the glucose sensor 120 may continuously monitor glucose levels of the patient, such that if the glucose sensor 120 determines glucose levels are outside a normal or desired range for the patient (e.g., glucose levels are too high or too low in the patient), the glucose sensor 120 may communicate that glucose levels are outside the normal or desired range to the device 104 (e.g., via the one or more processors) to signal for the device 104 to apply the stimulation/blocking therapy described herein to adjust glucose levels in the patient (e.g., mute the glycemic response to lower glucose levels in the patient, block insulin production in the patient as a possible technique to raise glucose levels in the patient, etc.).

As described herein, the system 100 and the corresponding stimulation/block therapy using the device 104, the wires 108, and the corresponding electrodes/electrode devices may be personalized for an individual patient. For example, personalization of the stimulation/block therapy may include adapting the stimulation/block therapy to a frequency that the patient uses the therapy and a lifestyle specific to the patient. Accordingly, the personalized therapy may be achieved based in part on using a machine learning algorithm that takes a set of inputs and continuously adapts, learns, and optimizes the output of the system 100 for the patient.

The machine learning algorithm may optimize one or more parameters for applying the therapy per patient. For example, the one or more parameters may include an optimization of a frequency, an amplitude, a ramp up, and a pattern of stimulation for the stimulation/block therapy specific to the patient. In some examples, a duty cycle (e.g., duration of applying the therapy to achieve a desired effect) for applying the therapy may also be optimized specific to the patient based on using the machine learning algorithm. Additionally, the machine learning algorithm may adapt the therapy to lifestyle preferences of the patient, such as levels of activity, nocturnal patterns, and circadian rhythm of the patient.

In some examples, one or more features may be utilized for training the machine learning algorithm described herein that is used to determine characteristics for optimally applying the therapy. For example, the one or more features may include one or more optimal stimulation parameters that achieve a desired level of glycemic reduction response in the patient. The one or more optimal stimulation parameters may include a frequency for the stimulation/block therapy, an amplitude for the stimulation/block therapy, a pulse width for the stimulation/block therapy, a shape of a waveform used for the stimulation/block therapy (e.g., a triangular wave, a square wave, a sine wave, a trapezoidal wave, etc.), a slope for a ramp up of the stimulation/block therapy (e.g., start with small amplitude and level off to an optimal level), a slope for a ramp down of the stimulation/block therapy (e.g., similar to the ramp up, but for termination of the therapy), or a combination thereof. Additionally or alternatively, the one or more features used to train the machine learning algorithm may include an average reduction in a post prandial glycemic peak given a known carbohydrate intake (e.g., in grams (g)).

In some examples, the patient may also provide one or more inputs to be used for the one or more features utilized for training the machine learning algorithm. For example, the patient may provide a level of patient satisfaction with current or previous parameters used when applying the therapy (e.g., as recorded via a patient-accessible application, such as recorded via a satisfaction assessment form provided in the application) and/or a level of patient comfort with current or previous parameters used when applying the therapy (e.g., as recorded via the patient-accessible application). Additionally or alternatively, the patient may provide one or more of a time of day when the patient ingests a meal, a type of food ingested with the meal (e.g., as measured by a carbohydrate count), activity levels of the patient, and results of an A1C test.

As an example, the patient may provide a first set of inputs specific to the patient (e.g., what food they ate, when they ate it, blood test results, activity levels, etc.). The machine learning algorithm may then determine a most optimal therapy (e.g., optimal parameters for the therapy, such as an optimal frequency, amplitude, ramp up, ramp down, duty cycle, etc.) to apply to the vagal trunks of the patient based on the first set of inputs after observing a first glycemic response corresponding to the first set of inputs. Subsequently, the patient may have a similar set of inputs at a future time (e.g., the patient eats a same type of food, eats at a similar time, etc. but on a different day in the future) but may experience a different glycemic response. Accordingly, the machine learning algorithm may be used to determine why the glycemic response was different for each situation (e.g., other features used for training the machine learning algorithm not explicitly input by the patient may be different for each glycemic response, such as sleep, exercise, other mediation changes, etc.), such that the machine learning algorithm can be updated or adapted based on the determined reason for the difference. As more inputs are gathered for training the machine learning algorithm, the machine learning algorithm may become more optimized for the patient, such that the glycemic response at all times of the day (particularly around meals) is the best possible individual response for that patient.

In some embodiments, the machine learning algorithm may also learn to identify situations where a stimulation/block therapy is not sufficient to control blood glucose levels of the patient and may signal an external system (or a wearable pump) of this 'breakthrough' situation to cause a dose of insulin to be added using the external system to mitigate residual blood sugar rise. Additionally, the machine learning algorithm may recommend a timing and dose of such a complementary medication so as to minimize risk of hypoglycemia or use of unnecessary insulin.

In some examples, the stimulation/block therapy may use a continuous glucose sensor (e.g., monitoring device that is configured to continuously monitor glucose levels in the patient) as an input to the optimization algorithm (e.g., the machine learning algorithm used to determine optimal settings or characteristics for applying the therapy). For example, the system 100 may optionally include the glucose sensor 120 that communicates (e.g., wirelessly) with other components of the system 100 (e.g., the device 104, the one or more processors, etc.) to provide inputs for training the machine learning algorithm. For example, the glucose sensor 120 may provide different direct or indirect features for training the machine learning algorithm, such as instantaneous glucose values, temporal glucose trends, glucose time in range, insulin sensitivity of the patient, a slope (e.g., time) for the glycemic response of the patient to come within an acceptable range after the therapy is activated, additional medication dosage used by the patient or applied to the patient, a duration of stimulation required to affect a desirable response, or a combination thereof.

Additionally or alternatively, one or more of the features used for training the machine learning algorithm may be determined from additional components of the therapy system provided herein, such as the patient-accessible application, the clinician user interface, or another component. Additionally, the features listed herein that are used for training the machine learning algorithm are not meant to be an exhaustive list of all features used to train the machine learning algorithm, and additional features may be used to train the machine learning algorithm not explicitly listed herein. In some examples, the machine learning algorithm may not need every feature listed herein to determine a good or optimal output for the therapy. For example, the machine learning algorithm may determine parameters for applying the therapy optimally based on the inputs and features that are present or received.

The system 100 or similar systems may be used, for example, to carry out one or more aspects of any of the methods 400, 500 and/or 600 described herein. The system 100 or similar systems may also be used for other purposes. It will be appreciated that the human body has many vagal nerves and the stimulation and/or blocking therapies described herein may be applied to one or more vagal nerves, which may reside at any location of a patient (e.g., lumbar, thoracic, etc.). Further, a sequence of stimulations and/or blocking therapies may be applied to different nerves. For example, a low frequency stimulation may be applied to a first nerve and a high frequency blockade may be applied to a second nerve.

Figure 2:
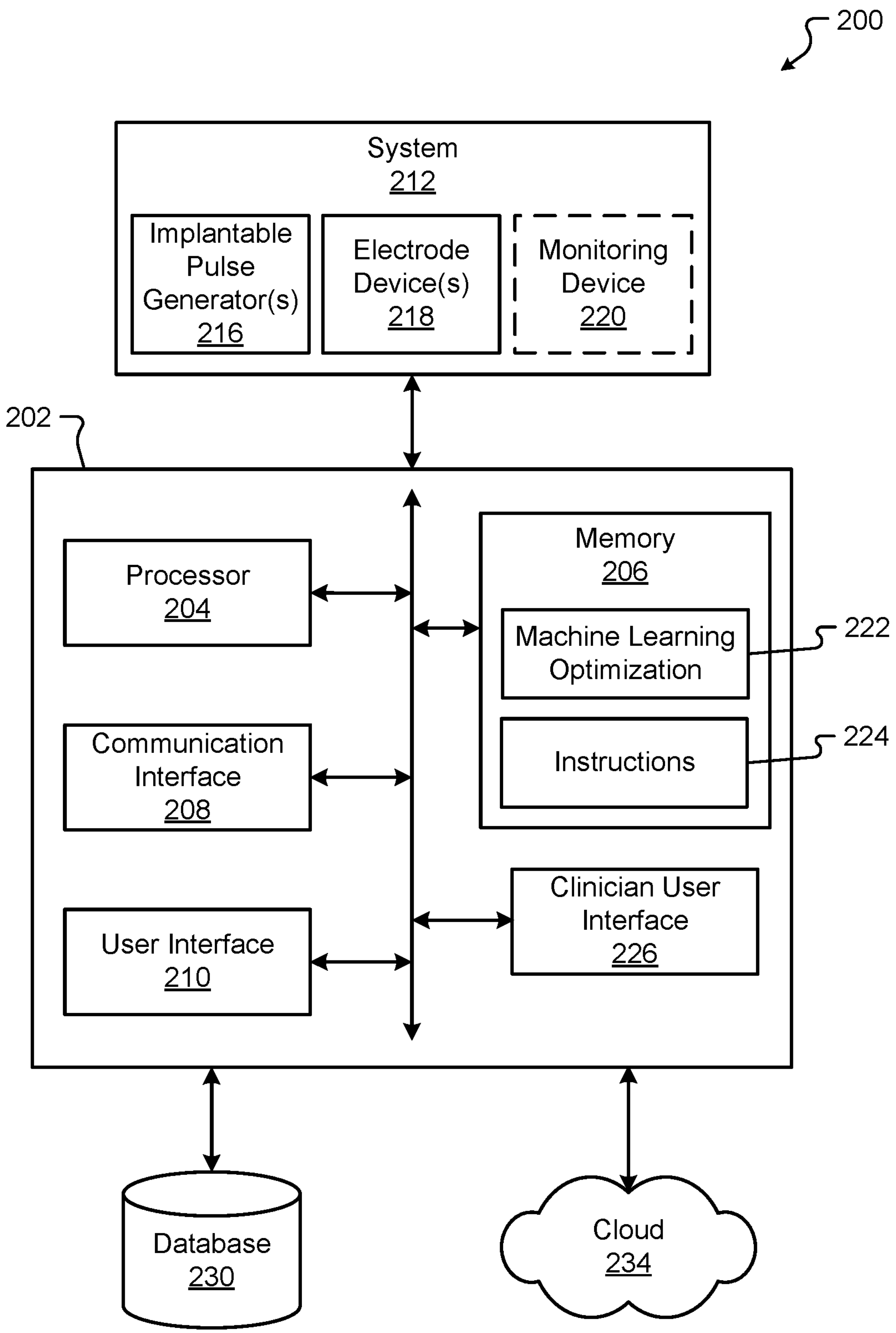
FIG. 2 is a block diagram of a system according to at least one embodiment of the present disclosure.

FIG. 2 depicts a block diagram of a system 200 according to at least one embodiment of the present disclosure is shown. In some examples, the system 200 may implement aspects of or may be implemented by aspects of FIG. 1 as described herein. For example, the system 200 may be used with an implantable pulse generator 216 and/or an electrode device 218, and/or carry out one or more other aspects of one or more of the methods disclosed herein. The implantable pulse generator 216 may represent an example of the device 104 or a component of the device 104 as described with reference to FIG. 1, where the electrode device 218 may represent the wires 108 and corresponding electrodes/cuff electrodes as described with reference to FIG. 1. Additionally or alternatively, the system 200 may be used with a monitoring device 220 and/or may carry out one or more other aspects of one or more of the methods disclosed herein. The monitoring device 220 may represent an example of the glucose sensor 112 as described with reference to FIG. 1. The system 200 comprises a computing device 202, a system 212, a database 230, and/or a cloud or other network 234. Systems according to other embodiments of the present disclosure may comprise more or fewer components than the system 200. For example, the system 200 may not include one or more components of the computing device 202, the database 230, and/or the cloud 234.

The system 212 may comprise the implantable pulse generator 216 and the electrode device 218. As previously described, the implantable pulse generator 216 may be configured to generate a current, and the electrode device 218 may comprise a plurality of electrodes configured to apply the current to an anatomical element. Additionally or alternatively, the system 212 may comprise the monitoring device 220 that is configured to continuously monitor glucose levels in the patient. The system 212 may communicate with the computing device 202 to receive instructions such as instructions 224 for applying a current to the anatomical element, where the current is intended to control a glycemic response of the patient. The system 212 may also provide data (such as data received from an electrode device 218 capable of recording data), which may be used to optimize the electrodes of the electrode device 218 and/or to optimize parameters of the current generated by the implantable pulse generator 216.

The computing device 202 comprises a processor 204, a memory 206, a communication interface 208, and a user interface 210. Computing devices according to other embodiments of the present disclosure may comprise more or fewer components than the computing device 202.

The processor 204 of the computing device 202 may be any processor described herein or any similar processor. The processor 204 may be configured to execute instructions 224 stored in the memory 206, which instructions may cause the processor 204 to carry out one or more computing steps utilizing or based on data received from the system 212, the database 230, and/or the cloud 234.

The memory 206 may be or comprise RAM, DRAM, SDRAM, other solid-state memory, any memory described herein, or any other tangible, non-transitory memory for storing computer-readable data and/or instructions. The memory 206 may store information or data useful for completing, for example, any steps of the methods 300, 400 and/or 500 described herein, or of any other methods. The memory 206 may store, for example, instructions and/or machine learning models that support one or more functions of the system 212. For instance, the memory 206 may store content (e.g., instructions 224 and/or machine learning models) that, when executed by the processor 204, cause the electrode device(s) 218 to apply a current to respective vagal trunks of the patient to optimally control a glycemic response of the patient and enable a machine learning optimization 222.

The machine learning optimization 222 enables the processor 204 to determine parameters for applying the current to the anatomical element of the patient that achieve a desired glycemic response in the patient using a machine learning algorithm. For example, the parameters determined through the machine learning optimization 222 may be considered optimal parameters for achieving the desired glycemic response. The desired glycemic response as described herein may correspond to a glycemic response the patient is satisfied and comfortable with, a glycemic response that includes a peak post prandial glycemic level that stays within an acceptable range (e.g., glycemic levels above this range may cause harm to the patient over time and glycemic levels below this range may cause hypoglycemia in the patient). The machine learning optimization 222 may use one or more features as described with reference to FIG. 1 to train the machine learning algorithm to determine the optimal parameters for achieving the desired glycemic response. For example, the machine learning algorithm may identify which parameters are used to apply the current to the anatomical element of the patient to achieve the desired glycemic response when a first set of inputs are present, such that those parameters can be used for subsequent applications of the current to the anatomical element if the first set of inputs or a substantially similar set of inputs are present for the patient.

The machine learning optimization 222 may also continually adapt and update the machine learning algorithm based on more inputs. For example, the machine learning algorithm may determine optimal parameters for applying the current to the anatomical element of the patient to achieve the desired glycemic response specific to whichever inputs are received prior to, during, and after the current is applied. Accordingly, the machine learning algorithm may attempt to use the same determined optimal parameters to apply the current whenever those same inputs or substantially similar inputs are received. However, in some examples, using the same optimal parameters for a same or substantially similar set of inputs may result in a different glycemic response of the patient that is suboptimal (e.g., glycemic levels in the patient go too high or go too low). In such examples, the machine learning optimization 222 may determine why the patient experienced a different glycemic response when the optimal parameters were used to apply the current to the anatomical element given the same or substantially similar set of inputs (e.g., another feature used to train the machine learning algorithm that is not explicitly input by the patient is different) and may update the machine learning algorithm based on the determined reason for the difference. As such, the machine learning optimization 222 continually adapts and updates the machine learning algorithm to ensure a desired glycemic response is achieved for the patient given a plurality of inputs and/or other factors.

In some examples, the system 200 may use the machine learning algorithm developed through the machine learning optimization 222 to detect situations where the result of applying the stimulation/block therapy is different enough from an expected result to represent a failure of the machine learning system or machine learning algorithm. In such examples where a failure of the machine learning algorithm is determined to be occurring, the system 200 may fall back to more conservative measures or more conservative parameters for applying the stimulation/block therapy until the discrepancy can be addressed (e.g., in a clinical setting).

That is, the system 200 may implement a quality control measure (e.g., inherent in the system 200) such that potential safety concerns from improperly operating machine learning algorithms can be detected and addressed safely.

Content stored in the memory 206, if provided as in instruction, may, in some embodiments, be organized into one or more applications, modules, packages, layers, or engines. Alternatively or additionally, the memory 206 may store other types of content or data (e.g., machine learning models, artificial neural networks, deep neural networks, etc.) that can be processed by the processor 204 to carry out the various method and features described herein. Thus, although various contents of memory 206 may be described as instructions, it should be appreciated that functionality described herein can be achieved through use of instructions, algorithms, and/or machine learning models. The data, algorithms, and/or instructions may cause the processor 204 to manipulate data stored in the memory 206 and/or received from or via the system 212, the database 230, and/or the cloud 234.

The computing device 202 may also comprise a communication interface 208. The communication interface 208 may be used for receiving data (for example, data from an electrode device 218 capable of recording data) or other information from an external source (such as the system 212, the database 230, the cloud 234, and/or any other system or component not part of the system 200), and/or for transmitting instructions, images, or other information to an external system or device (e.g., another computing device 202, the system 212, the database 230, the cloud 234, and/or any other system or component not part of the system 200). The communication interface 208 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 208 may be useful for enabling the device 202 to communicate with one or more other processors 204 or computing devices 202, whether to reduce the time needed to accomplish a computing-intensive task or for any other reason.

The computing device 202 may also comprise one or more user interfaces 210. The user interface 210 may be or comprise a keyboard, mouse, trackball, monitor, television, screen, touchscreen, and/or any other device for receiving information from a user and/or for providing information to a user. The user interface 210 may be used, for example, to receive a user selection or other user input regarding any step of any method described herein. Notwithstanding the foregoing, any required input for any step of any method described herein may be generated automatically by the system 200 (e.g., by the processor 204 or another component of the system 200) or received by the system 200 from a source external to the system 200. In some embodiments, the user interface 210 may be useful to allow the patient, a surgeon, or another user to modify instructions to be executed by the processor 204 according to one or more embodiments of the present disclosure, and/or to modify or adjust a setting of other information displayed on the user interface 210 or corresponding thereto.

Although the user interface 210 is shown as part of the computing device 202, in some embodiments, the computing device 202 may utilize a user interface 210 that is housed separately from one or more remaining components of the computing device 202. In some embodiments, the user interface 210 may be located proximate one or more other components of the computing device 202, while in other embodiments, the user interface 210 may be located remotely from one or more other components of the computer device 202.

In some examples, the machine learning algorithm described herein used to determine optimal parameters for applying the current to the anatomical element to achieve a desired glycemic response may be offloaded to the user interface 210 (e.g., or another user application accessible by the patient). Offloading the machine learning algorithm to the user interface 210 may provide battery savings for the implantable pulse generator 216 that would have otherwise stored the machine learning algorithm. The user interface 210 may allow for as much or as little engagement as the patient desires for training the machine learning algorithm. In some examples, the machine learning algorithm or component of the system described herein may be a fast train model (i.e., the use of the machine learning algorithm is intended to wean the patient off the application so that minimal interaction is required from the patient).

Additionally, in some examples, the computing device 202 may include a clinician user interface 226 (e.g., a second user application that is accessible by a medical professional or clinician responsible for initializing, implanting, and/or programming the implantable pulse generator 216). In some examples, the clinician user interface 226 may be intended to be an application-based module. Using the clinician user interface 226, a clinician or physician may determine and/or input settings for applying the current to the anatomical element of the patient. Additionally or alternatively, the clinician may determine or indicate the desired glycemic response for the patient using the clinician user interface 226, where the machine learning algorithm determines the optimal parameters for applying the current based on the desired glycemic response. In some examples, the clinician user interface 226 may also display metrics of system performance as the system optimizes the machine learning algorithm. For example, the clinician user interface 226 may display changes from baseline parameters for the stimulation/block therapy as the machine learning algorithm(s) learn, outlier events where the machine learning algorithm is not performing well, or other trends of performance that enable a clinician to make judgements about the outcomes and safety for the patient.

Similar to the user interface 210, although the clinician user interface 226 is shown as part of the computing device 202, in some embodiments, the computing device 202 may utilize a clinician user interface 226 that is housed separately from one or more remaining components of the computing device 202. In some embodiments, the clinician user interface 226 may be located proximate one or more other components of the computing device 202, while in other embodiments, the clinician user interface 226 may be located remotely from one or more other components of the computer device 202.

In some examples, the user interface 210 and/or the clinician user interface 226 may provide additional features to assist in the stimulation/block therapy described herein and for training the machine learning algorithm described herein. For example, the user interface 210 and/or the clinician user interface 226 may record feature settings for the stimulation/block therapy (e.g., which parameters are used for applying the current to the anatomical element, such as frequency, amplitude, waveform shape, pulse width, duty cycle, etc.), as well as recording patient feedback indicating a level of satisfaction or comfort the patient experiences when a given session of the stimulation/block therapy is applied. Accordingly, the recorded feature settings and patient feedback may be used (e.g., among other features/inputs as described above) to train the machine learning algorithm. Additionally, the user interface 210 and/or the clinician user interface 226 may record performance of the implantable pulse generator and the stimulation/block therapy (e.g., how a glycemic response of the patient is affected when the stimulation/block therapy is applied), such that results of the performance can be accessed or viewed by the patient and/or clinician to assist in adjusting therapy parameters and training the machine learning algorithm.

Additionally, the user interface 210 and/or the clinician user interface 226 may include a patient diary feature, a pattern/behavior prediction feature, a symptom bother scale feature, a device interrogation feature, a doctor messaging/electronic medical record (EMR) feature, a battery management feature, and/or additional features not listed herein. The patient diary feature may enable the patient to input (e.g., via a dropdown menu, manually typing, etc.) information associated with when the patient ingests a meal, what food was eaten with the meal, and/or other personal information specific to the patient. The pattern/behavior prediction feature may attempt to determine behaviors or patterns the patient exhibits, such as when the patient typically eats meals or when a glycemic response of the patient begins to increase, to predict when the stimulation/block therapy is to be applied. The symptom bother scale feature may enable the patient to input a level of satisfaction or comfort the patient experiences for a given set of parameters used to apply the stimulation/block therapy (e.g., too much stimulation can cause discomfort in the patient, where the symptom bother scale feature can be used to record the discomfort).

The device interrogation feature may enable the user interface 210 and/or the clinician user interface 226 to communicate (e.g., via near-field communication (NFC) and/or Bluetooth (BT) technology) with the device configured to apply the stimulation/block therapy (e.g., the implantable pulse generator) to record performance data of the device and/or feature settings used for applying the stimulation/block therapy. The doctor messaging/EMR feature may enable the machine learning algorithm to access anonymous patient data that can be used to assist in training the machine learning algorithm. The battery management feature may enable the user interface 210 and/or the clinician user interface 226 to transmit alerts to the patient and/or clinician for near end-of-life (EOL) for the device that is configured to apply the stimulation/block therapy (e.g., the implantable pulse generator) and/or other components used for applying the stimulation/block therapy. Additionally, the battery management feature may include a power saving mode that can be optionally implemented by the patient and/or clinician to extend operating life of the device and/or other components used for applying the stimulation/block therapy.

Though not shown, the system 200 may include a controller, though in some embodiments the system 200 may not include the controller. The controller may be an electronic, a mechanical, or an electro-mechanical controller. The controller may comprise or may be any processor described herein. The controller may comprise a memory storing instructions for executing any of the functions or methods described herein as being carried out by the controller. In some embodiments, the controller may be configured to simply convert signals received from the computing device 202 (e.g., via a communication interface 208) into commands for operating the system 212 (and more specifically, for actuating the implantable pulse generator 216 and/or the electrode device 218). In other embodiments, the controller may be configured to process and/or convert signals received from the system 212. Further, the controller may receive signals from one or more sources (e.g., the system 212) and may output signals to one or more sources.

The database 230 may store information such as patient data, results of a stimulation and/or blocking procedure, stimulation and/or blocking parameters, current parameters, electrode parameters, etc. The database 230 may be configured to provide any such information to the computing device 202 or to any other device of the system 200 or external to the system 200, whether directly or via the cloud 234. In some embodiments, the database 230 may be or comprise part of a hospital image storage system, such as a picture archiving and communication system (PACS), a health information system (HIS), and/or another system for collecting, storing, managing, and/or transmitting electronic medical records.

The cloud 234 may be or represent the Internet or any other wide area network. The computing device 202 may be connected to the cloud 234 via the communication interface 208, using a wired connection, a wireless connection, or both. In some embodiments, the computing device 202 may communicate with the database 230 and/or an external device (e.g., a computing device) via the cloud 234.

The system 200 or similar systems may be used, for example, to carry out one or more aspects of any of the methods 400, 500 and/or 600 as described herein. The system 200 or similar systems may also be used for other purposes.

Figure 3:
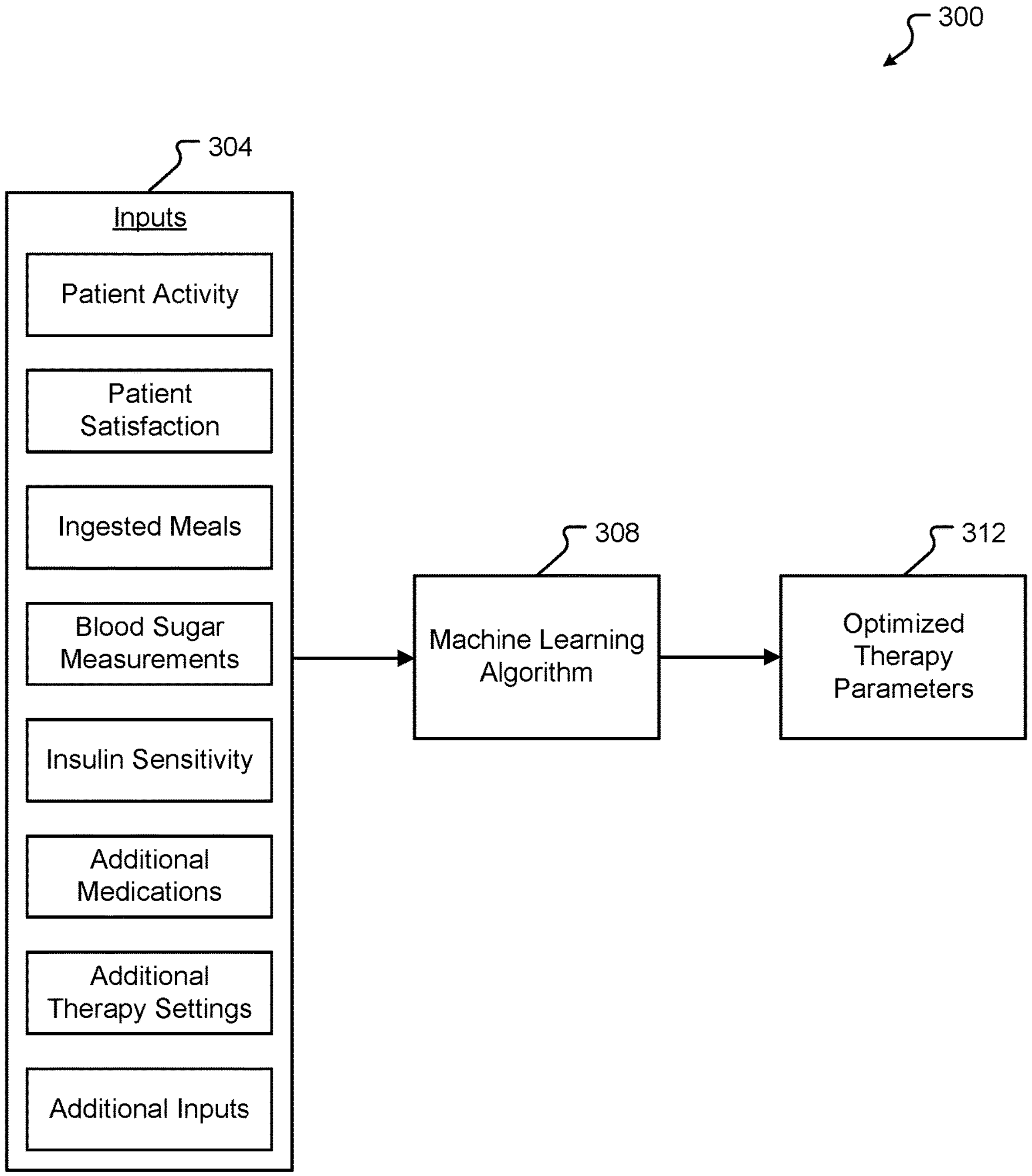
FIG. 3 is a block diagram of a machine learning system according to at least one embodiment of the present disclosure.

FIG. 3 depicts a block diagram of a machine learning system 300 in accordance with aspects of the present disclosure. The machine learning system 300 may implement aspects of or may be implemented by aspects of the system 100 and/or the system 200 as described with reference to FIGS. 1 and 2, respectively. For example, the machine learning system 300 may include a set of inputs 304 that are used to train a machine learning algorithm 308 to determine a set of optimized therapy parameters 312 for applying a stimulation/block therapy to an anatomical element of a patient as described herein to achieve glycemic control in the patient as a potential treatment for diabetes (e.g., type 2 diabetes more specifically). In some examples, the machine learning algorithm 308 may be an example of the machine learning algorithm as described with reference to FIGS. 1 and 2. Additionally, machine learning system 300 may include one or more components not explicitly listed or described herein that are used for training the machine learning algorithm 308 (e.g., processors, control devices, memory, user interfaces, implantable pulse generator, continuous glucose monitor, etc.).

The set of inputs 304 may include multiple features, parameters, factors, etc., that are used to train the machine learning algorithm 308. For example, the set of inputs 304 may include inputs associated with patient activity, patient satisfaction or comfort with a current or past set of parameters for the stimulation/block therapy, information associated with meals ingested by the patient, blood sugar measurements (e.g., input by the patient and/or retrieved from other devices, such as a continuous glucose monitor), insulin sensitivity of the patient, additional medications taken by the patient, additional settings for the stimulation/block therapy (e.g., settings that result in a desired glycemic response when the stimulation/block therapy is applied), and/or additional inputs not explicitly listed herein.

In some examples, the inputs associated with patient activity for the set of inputs 304 may include, and is not limited to, different parameters specific to the patient that are presently being used or have previously been used for the stimulation/block therapy, such as frequencies used for the stimulation aspect and the block aspect of the therapy, amplitudes used for the stimulation and block aspects, pulse widths used for the stimulation and block aspects, a waveform shape used for the stimulation aspect (e.g., triangular wave, square wave, sine wave, etc.), a slope for a ramp up of the therapy (e.g., the therapy starts with a small amplitude and increases before leveling off to an optimal level), a slope for a ramp down of the therapy (e.g., the therapy is applied with the amplitude at the optimal level or another value and decreases to zero or a minimal value for termination of the therapy), or a combination thereof. The inputs associated with patient activity may be input via the patient and/or a clinician via a respective user interface accessible by either. The patient satisfaction or comfort input for the current or past set of parameters used for the stimulation/block therapy of the set of inputs 304 may be recorded via an application associated with the therapy (e.g., via a user interface, such as the user interface 210 and/or clinician user interface 226 as described with reference to FIG. 2).

The inputs for the information associated with meals ingested by the patient may include a type of food ingested (e.g., as measured by carbohydrate count) and a time of day the patient ingested a corresponding meal. In some examples, the patient may manually input the type of food ingested (e.g., by selecting a picture of the food ingested, by inputting a carbohydrate count of the meal, by inputting other measurements associated with the meal, etc.) and the time of day that the meal was ingested (e.g., via an application or user interface described herein). Additionally, the inputs for the information associated with meals ingested by the patient may also include an average reduction in a post prandial glycemic peak given a known carbohydrate intake (e.g., in grams (g)), where the average reduction is determined based on a non-adjusted post prandial glycemic peak for that known carbohydrate intake when the stimulation/block therapy is not applied. The average reduction in post prandial glycemic peak may be determined from a continuous glucose monitor or based on glucose measurements input by the patient.

The blood sugar measurements of the set of inputs 304 may include, and is not limited to, results of an A1C test for the patient, instantaneous glucose measurements (e.g., autonomously received from a continuous glucose monitor, manually input by the patient from blood glucose tests self-administered by the patient such as via finger sticks, etc.), temporal glucose trends for the patient (e.g., how glycemic values of the patient have changed over time), glucose time in range for the patient (e.g., amount or percentage of time that blood glucose/blood sugar levels of the patient are within a target or desired range), etc. Additionally, the blood sugar measurements may include a slope or time for a glycemic response of the patient to come within a target or desired range after the stimulation/block therapy is activated or applied. The insulin sensitivity of the patient input of the set of inputs 304 may refer to or quantify how sensitive body cells of the patient are in response to insulin. For example, high insulin sensitivity may correspond to cells of the body using blood glucose more effectively, thereby reducing blood sugar, whereas low insulin sensitivity may correspond to cells not absorbing as much glucose, which can lead to high blood sugar levels. The insulin sensitivity may be input by the patient or the clinician (e.g., via an application or user interface as described herein). Additionally, the insulin sensitivity input may include categorical levels of insulin sensitivity for the patient (e.g., high, medium, low) or may be a quantitative measurement indicating the insulin sensitivity of the patient.

The additional medications input of the set of inputs 304 may include insulin injections the patient self-administers, other types of medications taken by the patient for other conditions experienced by the patient, etc. For example, the patient may input dosages of the additional medications taken (e.g., via the application or user interface as described herein) and/or a clinician may input information associated with the additional medications (e.g., via an application or clinician user interface as described herein). The additional therapy settings input of the set of inputs 304 may include, and is not limited to, a duration that the stimulation and/or blocking aspects of the therapy were applied to affect a desirable response in the patient (e.g., a desirable glycemic response), a stimulation pattern selection for the therapy, a count of a number of therapy or stimulation sessions applied to the patient, etc. The additional therapy settings may be recorded or input via an application or user interface described herein. For example, the application or user interface may be in communication with the implantable pulse generator that applies the therapy in the patient, such that the additional therapy settings can be captured autonomously by the application or user interface. Additionally or alternatively, the patient and/or clinician may manually input one or more of the additional therapy settings. In some examples, the manual inputs may be based on information captured by the application or user interface.

The additional inputs of the set of inputs 304 may include other inputs that potentially affect a glycemic response of the patient not listed in the examples above. For example, the additional inputs may include inputs indicating a posture of the patient, inputs indicating a level of exercise of the patient (e.g., captured by devices that measure factors corresponding to activity levels of the patient, such as an accelerometer), stress in the patient, amount of sleep, microbiome content, genetic components, comorbidities, macronutrients, and/or other inputs not explicitly listed or described herein. The additional inputs may be manually entered (e.g., by the patient or a clinician) or may be autonomously recorded by components of the machine learning system 300. In some examples, the additional inputs may also include anonymous patient data (e.g., stored in a database, such as the database 230 and/or cloud 234 as described with reference to FIG. 2) that indicates how different therapy settings affected a glycemic response for anonymous patients, which can be leveraged to train the personal machine learning algorithm specific to a given patient based on similarities between the given patient and the anonymous patients.

Subsequently, the set of inputs 304 may be used to train the machine learning algorithm 308 as described herein. In some examples, the machine learning algorithm 308 may be considered a machine learning-based adaptive algorithm configured for glycemic control. For example, the machine learning algorithm may be a personalized algorithm for a given patient, where different parameters for the stimulation/block therapy (e.g., including a frequency of the therapy, a pattern of for the stimulation(s), etc.) are learned from specific user experience for the given patient. In some examples, the machine learning algorithm may be trained to predict when a patient needs the stimulation/block therapy to be applied and when the patient does not need the stimulation/block therapy (e.g., to prolong battery life of the implantable pulse generator that is configured to apply a current to the anatomical element as part of the stimulation/block therapy). Accordingly, the machine learning algorithm 308 may be configured to find an optimal or best stimulation pattern (e.g., among other settings) for the given patient to affect a desired glycemic response as described herein.

The machine learning algorithm 308 may then generate the set of optimized therapy parameters 312 for applying the stimulation/block therapy after being trained using the set of inputs 304. In some examples, the set of optimized parameters 312 may be determined for the stimulation/block therapy based on optimizing the therapy on an optimal stimulation pattern (e.g., waveform shape, pulse width, frequency, amplitude, etc.), a desired glycemic response when the therapy is applied, a level of satisfaction and comfort reported by the patient for a given application of the therapy, etc. For example, the set of optimized therapy parameters 312 may include operational parameters of the stimulation/block therapy, such as signal frequency, signal type (e.g., square wave, sinusoidal wave, triangle wave, etc.), duty cycle, treatment duration, etc., that can be adjusted based on the set of inputs 304. Additionally, the set of optimized parameters 312 may be determined to minimize discomfort in the patient, minimize extra battery use (e.g., of the implantable pulse generator configured to apply the therapy), and/or a limited glycemic response after the therapy is applied.

Figure 4:
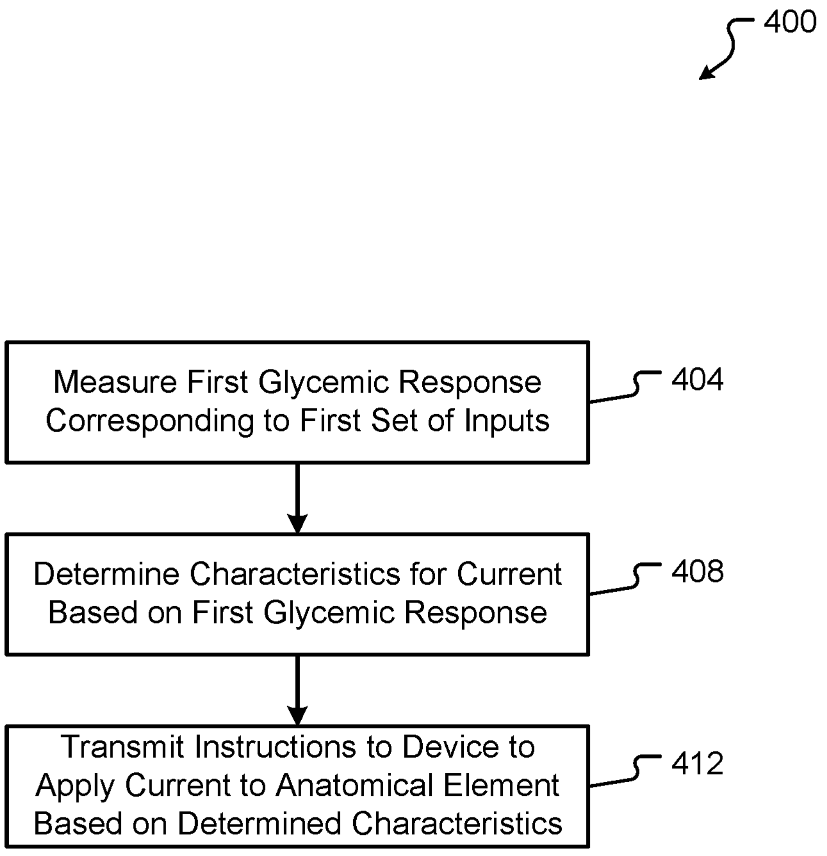
FIG. 4 is a flowchart according to at least one embodiment of the present disclosure.

FIG. 4 depicts a method 400 that may be used, for example, to determine optimal characteristics for applying a current to an anatomical element of a patient to achieve a desired glycemic response in the patient, where the optimal characteristics are determined based on a machine learning algorithm described herein.

The method 400 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 400. The at least one processor may perform the method 400 by executing elements stored in a memory (such as a memory in the device 104 as described above or a control unit). The elements stored in the memory and executed by the processor may cause the processor to execute one or more steps of a function as shown in method 400. One or more portions of a method 400 may be performed by the processor executing any of the contents of memory, such as providing a stimulation/block therapy and/or any associated operations as described herein.

The method 400 comprises measuring a first glycemic response for the patient, the first glycemic response corresponding to a first set of inputs at a first instance in time (step 404). For example, the patient may input (e.g., via a user application, such as the user interface 210) the first set of inputs, such as what time they digested a meal, a type of food ingested with the meal (e.g., as indicated based on a carbohydrate count for the meal), activity levels of the patient, etc. Accordingly, the at least one processor may then determine and/or measure a glycemic response for the patient that corresponds to the inputs received from the patient.

The method 400 also comprises determining, using the machine learning algorithm provided and described herein, one or more characteristics for applying the current to the anatomical element based on the first glycemic response (step 408). That is, the machine learning algorithm may be used to determine if characteristics that were used to apply the current to the anatomical element that resulted in the first glycemic response are optimal or not for achieving a desired glycemic response when the first set of inputs are present. For example, if the first glycemic response is different than the desired glycemic response, the machine learning algorithm may be updated to adjust one or more of the characteristics for applying the current if the first set of inputs or a substantially similar set of inputs are present prior to a subsequent application of the current. Additionally or alternatively, if the first glycemic response is the desired glycemic response, then the machine learning algorithm is not updated, and the characteristics used for applying the current to the anatomical element to achieve the first glycemic response with the first set of inputs present may be used for subsequent applications of the current to the anatomical element when the first set of inputs or a substantially similar set of inputs are present.

The method 400 also comprises transmitting instructions to a device (e.g., the device 104 as described with reference to FIG. 1 and/or the implantable pulse generator 216 as described with reference to FIG. 2) to apply the current to the anatomical element of the patient via a plurality of electrodes of an electrode device (e.g., the wires 108 and corresponding electrodes/cuff electrodes as described with reference to FIG. 1 and/or the electrode device 218 as described with reference to FIG. 2), where the current is applied to the anatomical element based on the machine learning algorithm that uses inputs gathered for determining the one or more characteristics for the current (step 412). For example, the device may be instructed to apply the current to the anatomical element using the one or more characteristics determined at step 408 if the first set of inputs or a substantially similar set of inputs are received prior to applying the current.

The present disclosure encompasses embodiments of the method 400 that comprise more or fewer steps than those described above, and/or one or more steps that are different than the steps described above.

Figure 5:
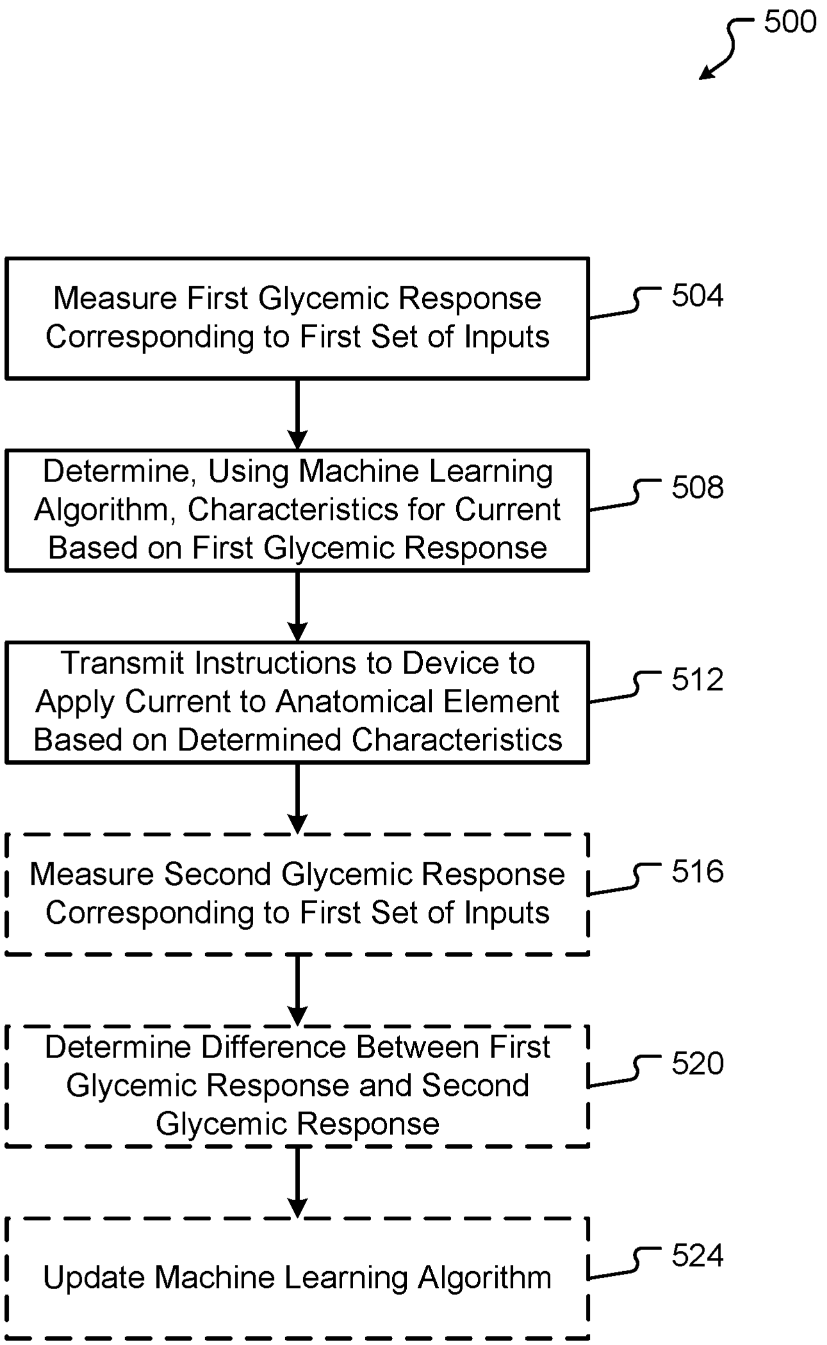
FIG. 5 is a flowchart according to at least one embodiment of the present disclosure.

FIG. 5 depicts a method 500 that may be used, for example, updating a machine learning algorithm that is used to determine optimal characteristics for applying a current to an anatomical element of a patient to achieve a desired glycemic response in the patient.

The method 500 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 500. The at least one processor may perform the method 500 by executing elements stored in a memory (such as a memory in the device 104 as described above or a control unit). The elements stored in the memory and executed by the processor may cause the processor to execute one or more steps of a function as shown in method 500. One or more portions of a method 500 may be performed by the processor executing any of the contents of memory, such as providing a stimulation/block therapy and/or any associated operations as described herein.

The method 500 comprises measuring a first glycemic response for the patient, the first glycemic response corresponding to a first set of inputs at a first instance in time (step 504). The method 500 also comprises determining, using the machine learning algorithm provided and described herein, one or more characteristics for applying the current to the anatomical element based on the first glycemic response (step 508). The method 500 also comprises transmitting instructions to a device to apply the current to the anatomical element of the patient via a plurality of electrodes of an electrode device, where the current is applied to the anatomical element based on the machine learning algorithm that uses inputs gathered for determining the one or more characteristics for the current (step 512). Steps 504, 508, and 512 may implement aspects of steps 404, 408, and 412, respectively, as described with reference to FIG. 4.

The method 500 also comprises measuring a second glycemic response for the patient, the second glycemic response corresponding to a substantially similar set of inputs to the first set of inputs occurring at a second instance in time, where the second glycemic response is different than the first glycemic response and the second instance in time is different than the first instance in time (step 516). For example, the patient may eat a same meal at an approximately same time that correspond to the first set of inputs but may experience a different glycemic response than had previously been observed.

The method 500 also comprises determining a difference between the first glycemic response and the second glycemic response (step 520). For example, the at least one processor may determine why the first glycemic response was different than the second glycemic response even though both glycemic responses correspond to substantially similar sets of inputs. In some examples, the difference may be attributed to other features that are used to train the machine learning algorithm that are not explicitly input by the patient, such as glucose levels in the patient prior to applying the current, other glucose readings for the patient, additional medications present in the patient, etc.

The method 500 also comprises update the machine learning algorithm to determine the one or more characteristics for the current based at least in part on the determined difference (step 524). That is, based on the determined difference, the machine learning algorithm may be further trained and/or updated to determine which characteristics should be used for applying the current to the anatomical element in subsequent uses of the therapy to achieve a desired glycemic response in the patient.

The present disclosure encompasses embodiments of the method 500 that comprise more or fewer steps than those described above, and/or one or more steps that are different than the steps described above.

Figure 6:
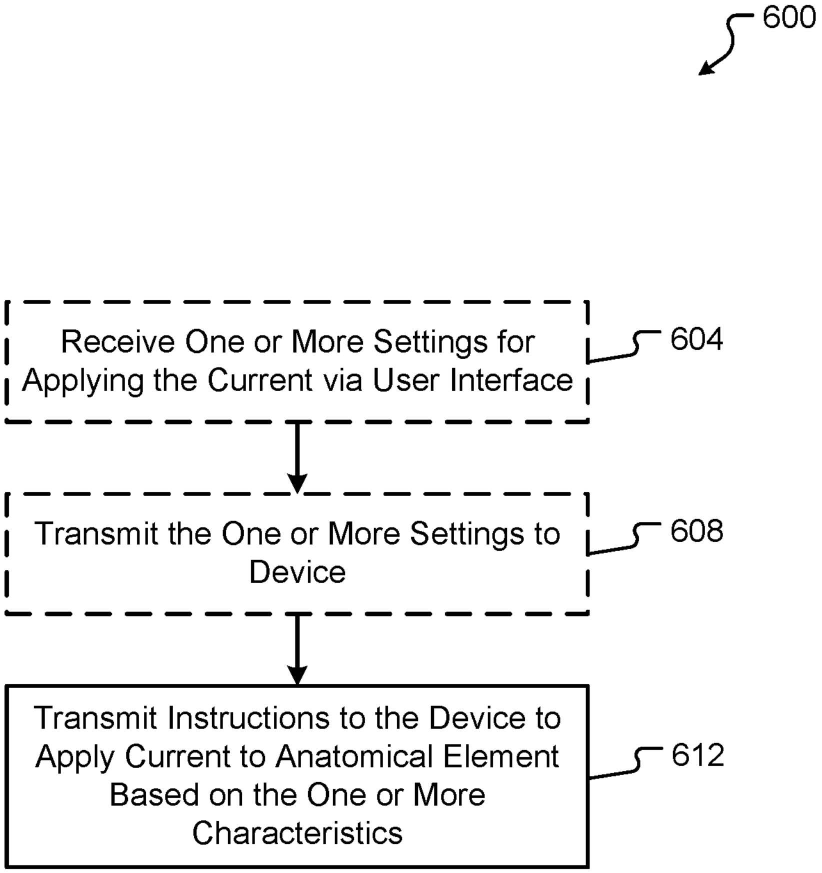
FIG. 6 is a flowchart according to at least one embodiment of the present disclosure.

FIG. 6 depicts a method 600 that may be used, for example, to receive settings for a machine learning algorithm that is used to determine optimal characteristics for applying a current to an anatomical element of a patient to achieve a desired glycemic response in the patient.

The method 600 (and/or one or more steps thereof) may be carried out or otherwise performed, for example, by at least one processor. The at least one processor may be the same as or similar to the processor(s) of the device 104 described above. The at least one processor may be part of the device 104 (such as an implantable pulse generator) or part of a control unit in communication with the device 104. A processor other than any processor described herein may also be used to execute the method 600. The at least one processor may perform the method 600 by executing elements stored in a memory (such as a memory in the device 104 as described above or a control unit). The elements stored in the memory and executed by the processor may cause the processor to execute one or more steps of a function as shown in method 600. One or more portions of a method 600 may be performed by the processor executing any of the contents of memory, such as providing a stimulation/block therapy and/or any associated operations as described herein.

The method 600 comprises receiving one or more settings for applying the current to the anatomical element via a user interface (step 604). For example, the user interface may be a user interface that is accessible by a clinical professional, such as the clinician user interface 226 as described with reference to FIG. 2. Accordingly, the one or more settings may be received from a clinical professional that is accessing the user interface. In some examples, the settings received from the clinical professional may be used for initializing and/or training the machine learning algorithm used to determine the optimal characteristics for applying the current to the anatomical element.

The method 600 also comprises transmitting the one or more settings to a device that generates the current to be applied to the anatomical element of the patient (e.g., the device 104 as described with reference to FIG. 1 and/or the implantable pulse generator 216 as described with reference to FIG. 2) (step 608). In some examples, the one or more settings may override characteristics that had previously been used to apply the current to the anatomical element of the patient (e.g., the one or more settings comprise the characteristics for the current). Additionally or alternatively, the one or more settings may be used to determine the characteristics with which the current is applied to the anatomical element of the patient (e.g., the one or more settings comprise desired glycemic response(s) for the patient, such that the characteristics are determined to achieve the desired glycemic response(s)).

The method 600 also comprises transmitting instructions to the device to apply the current to the anatomical element of the patient via a plurality of electrodes of an electrode device (e.g., the wires 108 and corresponding electrodes/cuff electrodes as described with reference to FIG. 1 and/or the electrode device 218 as described with reference to FIG. 2), where the current is applied to the anatomical element based at least in part on the machine learning algorithm that uses inputs gathered for determining the one or more characteristics for the current (step 612). In some examples, the current is applied to the anatomical element based on the one or more settings transmitted at step 508.

The present disclosure encompasses embodiments of the method 600 that comprise more or fewer steps than those described above, and/or one or more steps that are different than the steps described above.

As noted above, the present disclosure encompasses methods with fewer than all of the steps identified in FIGS. 4, 5, and 6 (and the corresponding description of the methods 400, 500, and 600), as well as methods that include additional steps beyond those identified in FIGS. 4, 5, and 6 (and the corresponding description of the methods 400, 500, and 600). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for stimulating an anatomical element of a patient, comprising:

an implantable pulse generator configured to generate a current;

an electrode device electrically coupled to the implantable pulse generator, the electrode device comprising a plurality of electrodes configured for placement on or around the anatomical element of the patient;

a monitoring device to monitor glucose levels in the patient;

a processor; and a memory storing data for processing by the processor, the data, when processed, causes the processor to:

determine one or more characteristics for the current based at least in part on a machine learning algorithm that uses a first set of gathered inputs from a first user interface, wherein the machine learning algorithm is stored on the first user interface;

transmit instructions to the implantable pulse generator to apply the current to the anatomical element of the patient via the plurality of electrodes of the electrode device in response to the one or more determined characteristics from the machine learning algorithm;

measure a plurality of glycemic responses for the patient based on outputs from the monitoring device;

determine a difference between the plurality of measured glycemic responses based at least in part on the first set of gathered inputs from the first user interface and a second set of gathered inputs not from the first user interface; and update the machine learning algorithm to determine one or more updated characteristics for the current based at least in part on the determined difference between the plurality of glycemic responses, the first set of gathered inputs, and the second set of gathered inputs.

2. The system of claim 1, wherein the memory stores further data for processing by the processor that, when processed, causes the processor to:

measure a first glycemic response for the patient, the first glycemic response corresponding to a first set of inputs at a first instance in time; and determine, using the machine learning algorithm, the one or more characteristics for the current based at least in part on the first glycemic response; and measure a second glycemic response for the patient, the second glycemic response corresponding to a substantially similar set of inputs to the first set of inputs occurring at a second instance in time, wherein the second glycemic response is different than the first glycemic response and the second instance in time is different than the first instance in time.

3. The system of claim 1, wherein the machine learning algorithm detects an insufficient glycemic response from the patient based on the plurality of glycemic responses for the patient and signals a patient wearable device to provide a determined dose of insulin to the patient at a determined instance of time.

4. The system of claim 1, wherein the first user interface is in communication with at least the implantable pulse generator and the processor, wherein the memory stores further data for processing by the processor that, when processed, causes the processor to:

receive one or more first inputs from the patient via the first user interface, wherein the one or more first inputs are used to train the machine learning algorithm to determine the one or more characteristics for the current based at least in part on a glycemic response of the patient corresponding to the one or more first inputs; and transmit the one or more characteristics for the current to the implantable pulse generator, wherein the current is applied to the anatomical element based at least in part on transmitting the one or more characteristics.

5. The system of claim 4, further comprising:

a second user interface accessible by a clinical professional, the second user interface in communication with the first user interface, the implantable pulse generator, the processor, or a combination thereof, wherein the memory stores further data for processing by the processor that, when processed, causes the processor to:

receive one or more settings for applying the current to the anatomical element from the clinical professional via the second user interface; and transmit the one or more settings to the implantable pulse generator, wherein the current is applied to the anatomical element based at least in part on transmitting the one or more settings.

6. The system of claim 4, wherein the one or more first inputs comprise a level of patient satisfaction with the current that is applied based at least in part on the one or more characteristics, a level of patient comfort with the current that is applied based at least in part on the one or more characteristics, a time of day when the patient ingests a meal, a type of food ingested with the meal, an amount of activity levels for the patient, results of an A1C test for the patient, additional medication dosages used by the patient, or a combination thereof.

7. The system of claim 1, wherein the monitoring device produces one or more outputs that comprise an average reduction in post prandial glycemic peak given a known intake of carbohydrates, instantaneous glucose measurements, temporal glucose trends, glucose time in range, insulin sensitivity of the patient, a slope or time for a glycemic response of the patient to come within an acceptable range after the current is applied to the anatomical element, a duration of applying the current to the anatomical element to effect a desirable glycemic response, or a combination thereof.

8. The system of claim 1, wherein the one or more characteristics of the current determined by the machine learning algorithm comprise an optimized frequency, amplitude, pulse width, shape of a waveform, slope for ramp up, slope for ramp down, pattern, duty cycle, or a combination thereof for the current.

9. The system of claim 1, wherein the one or more characteristics for the current are determined specific to the patient.

10. The system of claim 1, wherein the machine learning algorithm comprises a fast train machine learning model, a linear regression model, or a combination thereof.

11. The system of claim 1, wherein the anatomical element comprises a celiac vagal trunk and a hepatic vagal trunk of the patient.

12. The system of claim 1, wherein the current being applied to the anatomical element results in a reduced glycemic response in the patient.

13. The system of claim 1, wherein the second set of gathered inputs comprises at least one of monitored glucose levels of the patient prior to applying the current to the anatomical element, monitored glucose levels of the patient after applying the current to the anatomical element, and medications present in the patient.

14. A system for stimulating an anatomical element of a patient, comprising:

an implantable pulse generator configured to generate a current;

an electrode device comprising:

a body; and a plurality of electrodes disposed on the body and configured to apply the current to the anatomical element;

a monitoring device to monitor glucose levels in the patient;

a processor; and a memory storing data for processing by the processor, the data, when processed, causes the processor to:

determine one or more characteristics for the current based at least in part on a machine learning algorithm that uses a first set of gathered inputs from a first user interface, wherein the machine learning algorithm is stored on the first user interface;

transmit instructions to the implantable pulse generator to apply the current to the anatomical element of the patient via the plurality of electrodes of the electrode device in response to the one or more determined characteristics from the machine learning algorithm;

measure a plurality of glycemic responses for the patient based on outputs from the monitoring device;

determine a difference between the plurality of glycemic responses based at least in part on the first set of gathered inputs from the first user interface and a second set of gathered inputs not from the first user interface; and update the machine learning algorithm to determine one or more updated characteristics for the current based at least in part on the determined difference between the plurality of glycemic responses, the first set of gathered inputs, and the second set of gathered inputs.

15. The system of claim 14, wherein the memory stores further data for processing by the processor that, when processed, causes the processor to:

measure a first glycemic response for the patient, the first glycemic response corresponding to a first set of inputs at a first instance in time; and determine, using the machine learning algorithm, the one or more characteristics for the current based at least in part on the first glycemic response.

16. The system of claim 15, wherein the memory stores further data for processing by the processor that, when processed, causes the processor to:

measure a second glycemic response for the patient, the second glycemic response corresponding to a substantially similar set of inputs to the first set of inputs occurring at a second instance in time, wherein the second glycemic response is different than the first glycemic response and the second instance in time is different than the first instance in time.

17. The system of claim 14, wherein the first user interface is in communication with at least the implantable pulse generator and the processor, wherein the memory stores further data for processing by the processor that, when processed, causes the processor to:

receive one or more first inputs from the patient via the first user interface, wherein the one or more first inputs are used to train the machine learning algorithm to determine the one or more characteristics for the current based at least in part on a glycemic response of the patient corresponding to the one or more first inputs; and transmit the one or more characteristics for the current to the implantable pulse generator, wherein the current is applied to the anatomical element based at least in part on transmitting the one or more characteristics.

18. The system of claim 17, further comprising:

a second user interface accessible by a clinical professional, the second user interface in communication with the first user interface, the implantable pulse generator, the processor, or a combination thereof, wherein the memory stores further data for processing by the processor that, when processed, causes the processor to:

receive one or more settings for applying the current to the anatomical element from the clinical professional via the second user interface; and transmit the one or more settings to the implantable pulse generator, wherein the current is applied to the anatomical element based at least in part on transmitting the one or more settings.

19. A system for stimulating an anatomical element of a patient, comprising:

a first user interface;

an implantable pulse generator configured to generate a current; and an electrode device comprising:

a body; and a plurality of electrodes disposed on the body and configured to apply the current to the anatomical element, wherein the current is applied to the anatomical element based at least in part on a machine learning algorithm, wherein the machine learning algorithm is stored on the first user interface, that determines one or more characteristics for the current based on:

a determined difference between a plurality of glycemic responses for the patient based at least in part on a first set of gathered inputs from the first user interface and a second set of gathered inputs not from the first user interface.

20. The system of claim 19, wherein the first user interface is accessible by the patient to provide inputs for training the machine learning algorithm; and a second user interface accessible by a clinical professional, wherein the clinical professional provides settings via the second user interface for training the machine learning algorithm, determining the one or more characteristics of the current, or a combination thereof.

* * * * *